(12) United States Patent
Bray et al.

(10) Patent No.: US 6,406,903 B2
(45) Date of Patent: *Jun. 18, 2002

(54) DYNAMICALLY CONTROLLED CRYSTAL GROWTH SYSTEM

(75) Inventors: Terry L. Bray, Hoover; Larry J. Kim, Birmingham; Michael Harrington, Birmingham; Lawrence J. DeLucas, Birmingham, all of AL (US)

(73) Assignee: University of Alabama at Birmingham, Birmingham, AL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/131,729

(22) Filed: Aug. 10, 1998

Related U.S. Application Data

(63) Continuation of application No. 08/719,481, filed on Sep. 25, 1996, now abandoned.
(60) Provisional application No. 60/004,267, filed on Sep. 25, 1995.

(51) Int. Cl.$^7$ ................................................. C12N 7/00
(52) U.S. Cl. ................ 435/235.1; 435/239; 435/283.1; 117/69; 117/70; 117/202; 117/901; 117/925
(58) Field of Search ............................ 117/69, 70, 202, 117/901, 925; 435/235.1, 239, 283.1

(56) References Cited

U.S. PATENT DOCUMENTS

| | | | |
|---|---|---|---|
| 4,517,048 A | * | 5/1985 | Schlichta |
| 4,755,363 A | * | 7/1988 | Fujita et al. |
| 4,919,899 A | | 4/1990 | Herrmann et al. |
| 5,013,531 A | | 5/1991 | Snyder et al. |

FOREIGN PATENT DOCUMENTS

| | | | |
|---|---|---|---|
| JP | 63201098 | * | 8/1988 |
| JP | 06116098 | * | 4/1994 |

OTHER PUBLICATIONS

Alexander McPherson; "Preparation and Analysis of Protein Crystals"; 1982; Robert E. Krieger Publishing Co., Inc.; pp. 96–97.

H. Wilson Smith, et al.; "A method for programmable control of reservoir concentrations for protein crystal growth"; *Journal of Crystal Growth*; 1991; pp. 137–141.

L.J. Wilson, et al.; "Control of solvent evaporation in hen egg white lysozyme crystallization"; *Journal of Crystal Growth*; 1991; pp. 414–420.

E.N. Baker et al.; "X–ray Diffraction Data on Some Crystalline Varieties of Insulin"; *J. Mol. Biol.*; 1970; pp. 605–609.

D.M. Shotton et al.; "Crystalline Porcine Pancreatic Elastase"; *J. Mol. Biol.*; 1968; pp. 155–156.

Albert W. Hanson, et al.; "X–ray Studies on Single Crystals of *Escherichia Coli* Alkaline Phosphatase"; *J. Biol. Chem.*; Oct. 10, 1970; vol. 245, pp. 4975–4976.

Alexander McPherson, et al.; "X–ray crystallographic analysis of swine pancreas α–amylase"; *Biochimica et Biophysica Acta*; 1972; pp. 493–497.

Elizabeth Cacioppo, et al.; "Protein solubilities determined by a rapid technique and modification of that technique to a micro–method"; *Journal of Crystal Growth*; 1991; pp. 66–71.

Jean–Luc Eisele; "Preparation of Protein Crystallization Buffers with a Computer–Controlled Motorized Pipette"; *J. Appl. Cryst.*; 1993; pp. 92–96.

M. Jane Cox, et al.; "An Investigation of Protein Crystallization Parameters Using Successive Automated Grid Searches (SAGS)"; *Journal of Crystal Growth*; pp. 318–324.

Naomi E. Chayen; "An Automated System for Micro–Batch Protein Crystallization and Screening"; *J. Appl. Cryst*; pp. 297–302.

L.J. Wilson, et al.; "Crystallization of proteins by dynamic control of evaporation"; *Journal of Crystal Growth*; pp. 142–147.

(List continued on next page.)

Primary Examiner—Leon B. Lankford, Jr.
(74) Attorney, Agent, or Firm—Merchant & Gould P.C.

(57) ABSTRACT

Crystal growth can be initiated and controlled by dynamically controlled vapor diffusion or temperature change. In one aspect, the present invention uses a precisely controlled vapor diffusion approach to monitor and control protein crystal growth. The system utilizes a humidity sensor and various interfaces under computer control to effect virtually any evaporation rate from a number of different growth solutions simultaneously by means of an evaporative gas flow. A static laser light scattering sensor can be used to detect aggregation events and trigger a change in the evaporation rate for a growth solution. A control/follower configuration can be used to actively monitor one chamber and accurately control replicate chambers relative to the control chamber. In a second aspect, the invention exploits the varying solubility of proteins versus temperature to control the growth of protein crystals. This system contains miniature thermoelectric devices under microcomputer control that change temperature as needed to grow crystals of a given protein. Complex temperature ramps are possible using this approach. A static laser light scattering probe also can be used in this system as a non-invasive probe for detection of aggregation events. The automated dynamic control system provides systematic and predictable responses with regard to crystal size. These systems can be used for microgravity crystallization projects, for example in a space shuttle, and for crystallization work under terrestial conditions. The present invention is particularly useful for macromolecular crystallization, e.g. for proteins, polypeptides, nucleic acids, viruses and virus particles.

17 Claims, 33 Drawing Sheets

OTHER PUBLICATIONS

G.A. Casay, et al.; "Laser scattering in a hanging drop vapor diffusion apparatus for protein crystal growth in a microgravity environment"; *Journal of Crystal Growth*; 1991; pp. 95–101.

William W. Fowlis, et al.; "Experimental and Theoretical Analysis of the Rate of Solvent Equilibration in the Hanging Drop Method of Protein Crystal Growth"; *Journal of Crystal Growth*; 1988; pp. 117–129.

Marjorie M. Harding, et al.; "The Crystal Structure of Insulin"; *J. Mol. Biol.*; 1966; pp. 212–226.

* cited by examiner

LINBRO BOX HANGING DROP VAPOR DIFFUSION CHAMBER.

DROP VOLUME VERSUS TIME FOR A TYPICAL VAPOR DIFFUSION
EXPERIMENT IN A LINBRO BOX.

FIG. 4    DYNAMICALLY CONTROLLED VAPOR DIFFUSION SYSTEM.

CLOSE-UP OF TEN CHAMBER GROUP.

SIZE AND NUMBER OF MACROCRYSTALS OBTAINED FROM LINEAR EVAPORATION PROFILES WITH LINBRO CONTROLS

NOTE: CRYSTAL MEASUREMENTS WERE RECORDED FOR EACH PROFILE AFTER REACHING IDENTICAL FINAL DROP VOLUMES

SIZE AND NUMBER OF MACROCRYSTALS OBTAINED FROM LINEAR EVAPORATION PROFILES WITH LINBRO CONTROLS.

NOTE: CRYSTAL MEASUREMENTS WERE RECORDED FOR EACH PROFILE AFTER REACHING IDENTICAL FINAL DROP VOLUMES

DETECTION OF NUCLEATION BY LASER LIGHT SCATTERING AND RESPONSE BY MODIFYING THE RATE OF INCREASE IN σ.

• THE EVAPORATION PROFILE WAS MODIFIED IN RESPONSE TO NUCLEATION DETECTION

LYSOZYME CRYSTAL GROWTH AT DIFFERENT EVAPORATION RATES, TRIGGERED AND NON-TRIGGERED.

DYNAMICALLY CONTROLLED TEMPERATURE SYSTEM SCHEMATIC.

LASER LIGHT SCATTERING SCHEMATIC WITH NUCLEATION CHAMBER.

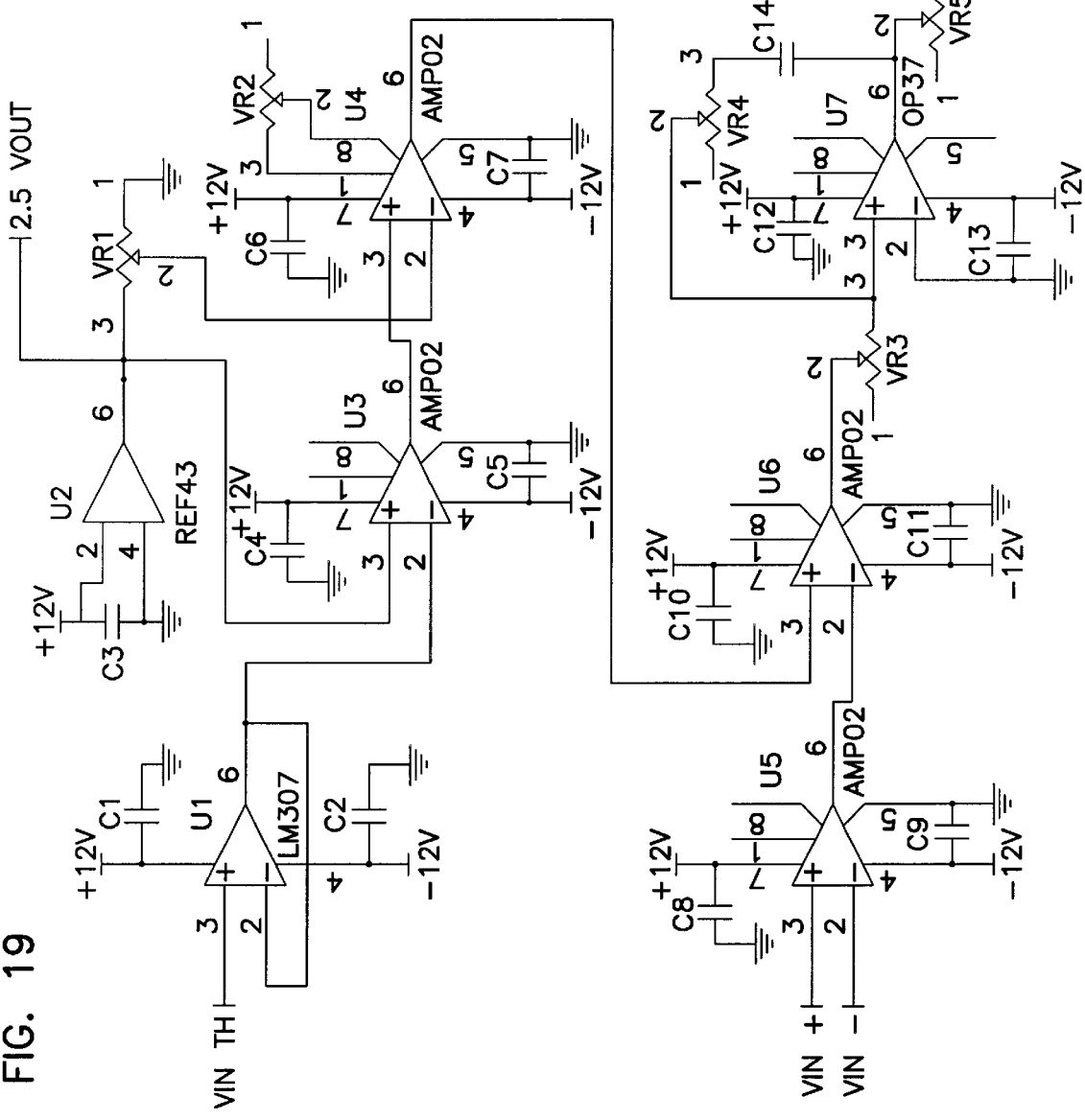
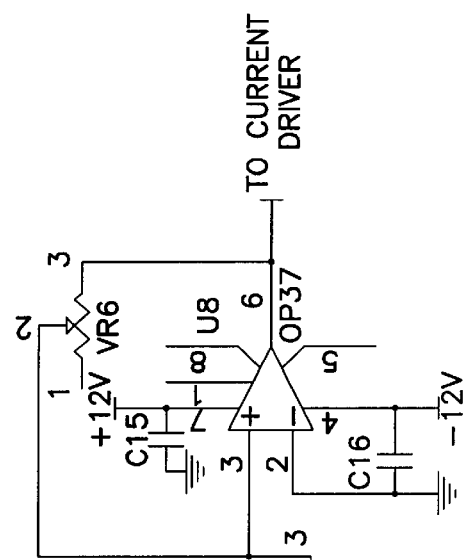
FIG. 19

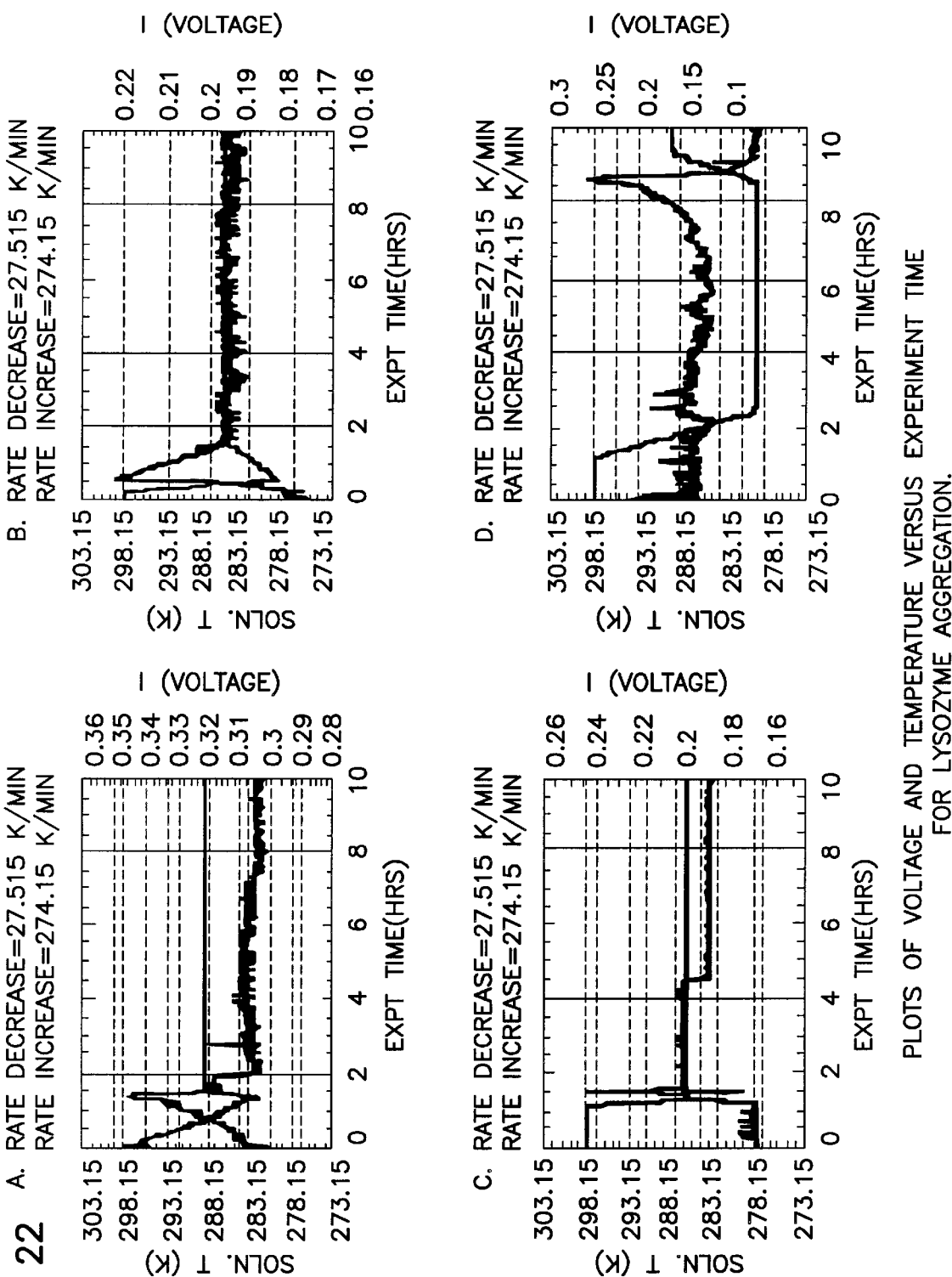

Rate Decrease = 27.515 K/min
Rate Increase = 274.15 K/min

Rate Decrease = 274.15 K/min
Rate Increase = 27.415 K/min

Rate Decrease = 274.15 K/min
Rate Increase = 274.15 K/min

Rate Decrease = 27.515 K/min
Rate Increase = 27.515 K/min

PLOTS OF VOLTAGE AND SOLUTION TEMPERATURE VERSUS EXPERIMENT TIME FOR BOVINE INSULIN AGGREGATION.

PLOTS OF VOLTAGE AND TEMPERATURE VERSUS EXPERIMENT TIME FOR PORCINE INSULIN AGGREGATION.

TEMPERATURE CONTROL/FOLLOWER RESULTS

CONTROL/FOLLOWER EXPERIMENT WITH LYSOZYME PROTEIN. CONCENTRATION IS 60 mg/ml WITH 2.0% NaCl. TEMPERATURE RAMP RATE IS 0.5 °C/min. PLOT OF GROWTH OF CRYSTALS VS. TIME.

CONTROL/FOLLOWER EXPERIMENT WITH LYSOZYME PROTEIN. CONCENTRATION IS 60 mg/ml WITH 2.0% NaCl. TEMPERATURE RAMP RATE IS 0.5 °C/min. GRAPH OF POPULATION IN INDIVIDUAL CELLS.

DYNAMICALLY CONTROLLED CRYSTAL GROWTH SYSTEM

This application is a continuation of application Ser. No. 08/719,481, filed Sep. 25, 1996 now abandoned, based on provisional application Ser. No. 60/004,267, filed Sep. 25, 1995, which applications are incorporated herein by reference.

GOVERNMENT CONTRACT INFORMATION

The work reflected in this application was supported by NASA contract NAS8-40189.

BACKGROUND OF THE INVENTION

Protein structural information has proven beneficial for understanding structure/function relationships and for applications such as structure-based drug design. X-ray crystallography is the predominant technique used to obtain three-dimensional protein structure information. A critical component of this technique is the growth of high quality, well ordered crystals of the target protein. Advances in x-ray diffraction equipment, data collection methods, and computational capabilities have progressed to the point where the growth of high quality crystals is often the rate limiting step for the determination of three-dimensional protein structures. Many different techniques have been used in the attempt to grow high quality protein crystals. The most widely used protein crystal growth technique, vapor diffusion, utilizes a growth solution containing protein and a precipitating agent. A popular vapor diffusion configuration, typically described as the hanging-drop or Linbro method (McPherson, Jr., A. (1982), Preparation and Analysis of Protein Crystals (Wiley, New York)—see FIG. 1), uses a reservoir solution containing precipitant and a buffered protein/precipitant solution that "hangs" from a sealed cover slip positioned over the reservoir. The initial solution conditions are such that water vapor diffuses from the protein solution into the reservoir solution, thereby increasing the concentration of the protein beyond its solubility point. One significant limitation of the traditional vapor diffusion technique is that the evaporation of water from the growth solution (within a particular geometry) is fixed by the starting concentrations of the solution components (see FIG. 2). Thus, the rate at which the approach to supersaturation of the growth solution occurs is fixed, even if modification of this evaporation rate is desirable, and this technique suffers from the inability to control the vapor equilibration process once the experiment is initiated.

The vapor diffusion technique has been used successfully to grow protein crystals in the microgravity environment of NASA's Space Shuttle, with space flight hardware called the Vapor Diffusion Apparatus or VDA, (Herrmainn, F. T., and Herren, B. J. (1990) "Crystal Growth Apparatus", U.S. Pat. No. 4,919,899 and Snyder, R. S.; Herren, B. J.; Carter, D. C.; Yost, V. H.; Bugg, C. E.; DeLucas, L. J.; Suddath, F. L. (1991) "Macromolecular Growing Sytems", U.S. Pat. No. 5,013,531). The original Vapor Diffusion Apparatus (VDA) was used to grow protein crystals in the microgravity environment of NASA's Space Shuttle. However, its concept and design have proven not to be optimal and it has specific limitations. For example, during crystal growth and nucleation, the vapor diffusion profile is fixed by the starting solution concentrations. Also no modification of the experiment is possible and photography during crystal growth is sporadic and non-isothermal. Although significant, the results with the Vapor Diffusion Apparatus are not optimal as evidenced by the following statistics. Only 25% of all proteins flown in the VDA produced crystals that diffracted better than any crystals grown on Earth. 40% of protein flown produced crystals which did not diffract better and 35% produced no crystals. Clearly there is need for methods and devices to improve the success ratio. Also, investigations have been underway (Smith, H. W. & DeLucas, L. J. (1991), J. Crystal Growth 110 137; Wilson, L. J. & Suddath, F. L. (1992), J. Crystal Growth 116 414) in the attempt to produce systems that will allow control over the evaporation profile of a growth solution. Early experiments showed that simply slowing down the evaporation rate of a growth solution generally produces a smaller population of larger crystals than can be obtained with traditional vapor diffusion techniques. Recent results from a large number of experiments shows this effect to be consistent not only for lysozyme, but for other proteins as well.

While vapor diffusion has been (and still is) a very popular technique, it has not always proven to be the best method for a given protein, and hence a wide range of other approaches have been used as a means to obtain high quality protein crystals. Another protein crystal growth technique, temperature, has only begun to be extensively explored in recent years. This technique utilizes the variable solubility versus temperature that some proteins exhibit for a given solution condition as a means for initiating and controlling crystal growth. Though this approach offers promise when compared to other techniques for controlling the rate of growth to produce high quality protein crystals, this method is not without limitations. Several proteins have been crystallized successfully using temperature (Baker, E. N. and Dodson, G. (1970), J. Mol. Biol. 54, 605; Shotton, D. M., Hartley, B. S., Camerman, N. and Hofnab, T. (1968), J. Mol. Biol. 32, 155; Hanson, A. W., Applebury, M. L., Coleman, J. E. and Wyckoff, H. (1970), J. Biol. Chem. 245, 4975; McPherson, JR., A. and Rich, A. (1972), Biochem. Biophys. Acta 285, 493), and recent developments in custom instrumentation and devices that screen protein solubility versus temperature improve the usefulness of temperature as a strategic method for growing protein crystals (Cacioppo, E., Munson, S. and Pusey, M. L. (1991), J. Crystal Growth 110, 66).

Despite this, the approach to finding suitable conditions that yield high quality protein crystals predominantly has been a trial and error process, where more than one thousand crystallization conditions are typically screened, often without success. Several systems have been constructed to aid the growth of protein crystals. These systems vary in complexity from simple hand-held devices (Eisele, J.-L. (1993), J. Appl. Cryst. 26, 92) to complex robotic systems that simply prepare and monitor different conditions (Cox, M. J. and Weber, P. C. (1988), J. Crystal Growth 90, 318; Chayen, N. E., Stewart, P. D. S., Maeder, D. L. and Blow, D. M. (1990), J. Appl. Cryst. 23, 297). Only a few systems have attempted to achieve control over the dynamics of protein crystal growth (Wilson, L. J., Bray, T. L. and Suddath, F. L. (1991), J. Crystal Growth 110, 142; Casey, G. A. and Wilson, W. W. (1992), J. Crystal Growth 122, 95) by altering the rate at which water is removed from the growth solution. Other investigations have been underway (Smith, H. W. and DeLucas, L. J. (1991), J. Crystal Growth 110, 137; Wilson, L. J. and Suddath, F. L. (1992), J. Crystal Growth 116, 414) in the attempt to produce systems that will allow control over the evaporation profile of a growth solution. Early experiments showed that simply slowing down the evaporation rate of a growth solution generally produces a smaller population of larger crystals than can be obtained with traditional vapor diffusion techniques. However, they have not offered true dynamic control of the protein crystal growth process.

SUMMARY OF THE INVENTION

The present invention provides a system for dynamic control of crystal growth, particularly for difficult-to-crystallize macromolecular substances such as proteins, polypeptides, nucleic acids, viruses and virus fragments. The nucleic acids include DNA, RNA and fragments of DNA and RNA. While reference is made hereafter to protein crystal growth, it should be understood that these teachnigs will be equally applicable to other macromolecular substances. Dynamic control of protein crystal growth (DC/PCG) has operational advantages that include the ability to separate protein crystal aggregation and/or nucleation from the post nucleation protein crystal growth phase and the potential for limiting the number of nucleation sites. Supersaturation conditions necessary for the aggregation and /or nucleation of proteins are often significantly greater than those needed for subsequent growth of the crystal. In order to minimize problems during the subsequent growth phase caused by the higher supersaturation necessary for nucleation, it is desirable to separately control the nucleation and growth environments. With DC/PCG, one has the capability to vary post-nucleation growth kinetics. One also has the capability to optimize crystal growth conditions in subsequent experiments. With respect to microgravity experiments, DC/PCG also minimizes protein sample quantities and minimizes astronaut crew time in experiment operation.

The present invention provides systems with increased capacity and versatility for the growth of protein crystals by vapor diffusion or temperature. Temperature adjustments are advantageous in providing a non-invasive means of controlling the supersaturation environment of protein nuclei. Additionally, laser light scattering data from the growth medium allows the aggregation state of the protein to be evaluated non-invasively and provides for dynamic control of the crystallization process. These systems achieve truly dynamically controlled protein crystal growth system that can be used for both terrestrial and microgravity experiments.

BRIEF DESCRIPTION OF THE DRAWINGS

FIGS. 22(a)–(d) show plots of voltage and solution temperature versus experiment time for lysozyme crystals.

DETAILED DESCRIPTION

Figure 1:
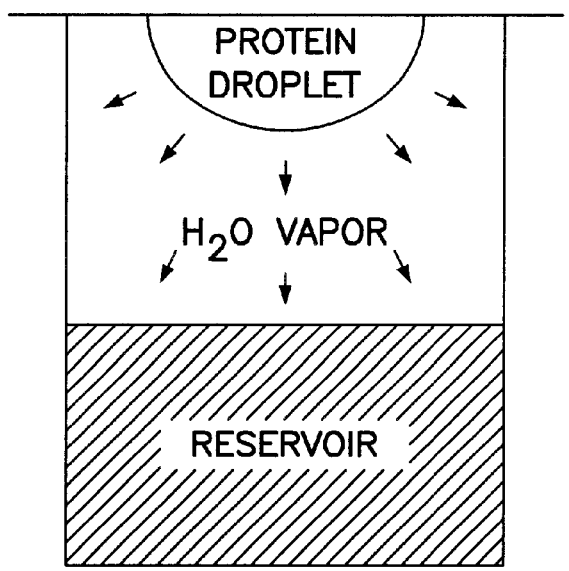
FIG. 1 illustrates a Linbro box hanging drop vapor diffusion chamber of the prior art.
Figure 2:
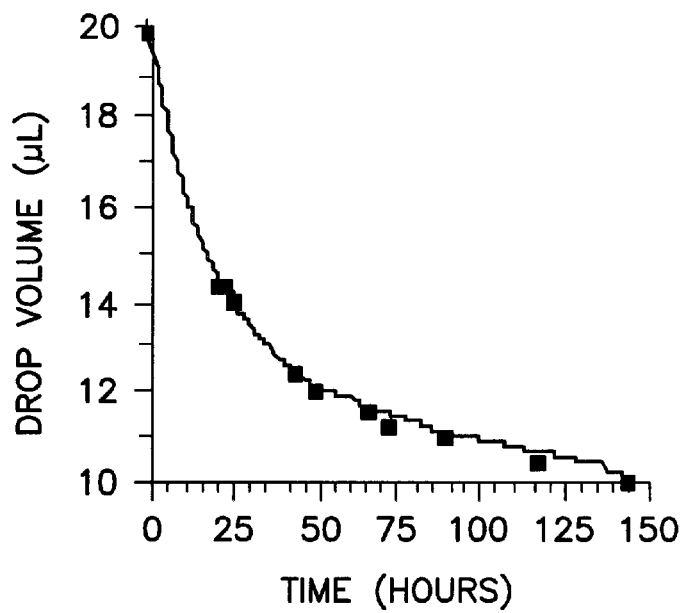
FIG. 2 is a graph showing drop volume versus time for a typical vapor diffusion experiment in a Linbro box.

The disclosure of U.S. Ser. No. 08/432,914 filed May 1, 1995 is incorporated herein by reference in its entirety.

The present invention is directed to a method and apparatus for the dynamic control of the crystal growth process. In particular, the present invention is directed to crystal growth systems based on vapor diffusion or temperature changes for initiating crystallization from a solution. While the present invention is useful for crystallization of inorganic and organic substances in general, the present invention is particularly useful for crystallization of macromolecular substances such as proteins, polypeptides, nucleic acids (for example DNA, RNA and fragment of DNA and RNA), viruses and virus fragments, especially proteins. The present invention is useful in crystallization studies for structure-based drug design targets and for determining structures of substances to be inhibited in treating diseases. In addition, the present invention is useful for work with complexes of various macromolecular substances, for example with inhibitors, and such related substances should be considered to included in the definition of the macromolecular substances.

Ordinarily, for macromolecular substances the substance to be crystallized will be dissolved in water, but the present invention is equally useful for other solvents as needed. The dynamic control of the present invention can be based on feedback obtained by observation of the solution being crystallized. Such feedback can be obtained by using monitoring techniques such as laser light scattering, real time video, turbidity measurements, interferometry, diffraction, ultrasonography, scintillation, polarization, schlieren optics, ellipsometry, holography and raman spectroscopy. It will be noted that some of these monitoring systems, e.g. laser light scattering, are not capable of distinguishing between aggregation and nucleation in the solution. This is not critical in the context of the present invention, and the detection of either event is suitable. The present invention can be used advantageously for microgravity crystallization work, for example in the Space Shuttle, as well as for terrestial work.

Vapor Diffusion Based Systems

The present invention can provide dynamic control for crystallization in the traditional "hanging drop" type configuration as well as in a "container" configuration. In each case, the solvent evaporation rate can be controlled carefully to respond to the progression of the crystallization. The solvent evaporation rate can be controlled by means of a variable gas flow. It is particularly desirable to avoid having the gas flow impinge directly upon the crystallization solution. One way to accomplish this is to have the crystallization reaction chamber separated into two sections, a solvent evaporation section and a purging section, separated by a barrier that substantially prevents direct impingement of the gas flow from the purging section on the crystallization solution but permits passage of solvent vapor. The rate of solvent evaporation from the crystallization solution can be controlled by varying the gas flow through the purging section.

The removal of solvent from the crystal growth solution can be checked by monitoring the gas removed from the purging section. In the case of an aqueous solvent, this can be done by monitoring the relative humidity of the purged gas. It is possible to multiplex a number of reaction chambers to one humidity sensor, allowing a large number of experiments to be performed simultaneously. It also is possible to handle a number of reaction chambers using a "control/follower" concept, where one chamber (the control) is monitored actively and other chambers (the followers) are acted upon in response to events occurring in the control chamber. A static laser light scattering system is one example of a useful a sensor for detecting aggregation events occurring in growth solutions to trigger a response, such as changing the evaporation rate of one or more of the crystal growth solutions. Laser light scattering is an important diagnostic tool to monitor protein crystal nucleation. It constitutes a sensitive, nonintrusive and real-time diagnostic for dynamic control of protein crystal growth. It can be adapted for most protein crystal growth configurations and can provide predictive information important to protein crystal growth.

A first example of a dynamically controlled vapor diffusion system (DCVDS) is based on the "hanging drop" vapor diffusion methods that have yielded relatively high success rates for obtaining protein crystals. This system incorporates a controlled flow of gas, dry nitrogen ($N_2$) gas as one example, instead of a reservoir solution to extract water, via the vapor phase, from the growth solution. This allows precise control over the rate at which the growth solution "equilibrates." In the traditional "hanging drop" vapor diffusion experiment, water diffuses rapidly during the early stages of the experiment and subsequently slows down asymptotically as the experiment progresses. Depending upon the solution components, complete equilibration can occur over a range of 3 to 30 days (Fowlis et al., (1988), J. Crystal Growth 90, 117). The present system described allows the equilibration rate to be varied at virtually any rate. While nitrogen gas is useful, other gases can be used as desired, and examples include non-reactive gases such as He, Ne, Xe, Ar and Kr. In addition, other gases such as $CO_2$ can be used if they do not have an adverse impact on the solution being crystallized, or if measures are taken to reduce any adverse impact such as buffering against pH changes.

Figure 3:
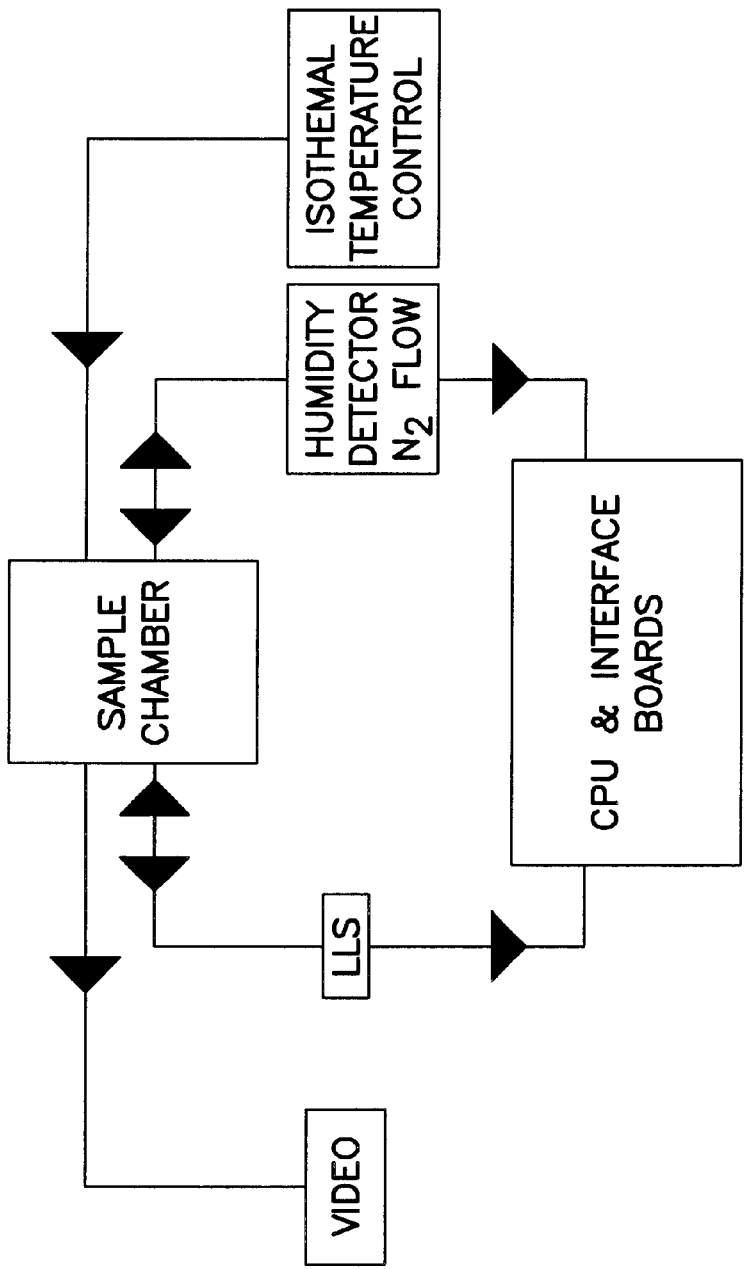
FIG. 3 is a block diagram of an example for dynamic control protein crystal growth (DC/PCG) via vapor diffusion with evaporation rate controlled by nitrogen gas flow.

FIG. 3 is a block diagram of a suitable system for protein crystal growth effected by vapor diffusion with nitrogen gas to control the evaporation rate. The sample chamber can be instrumented with laser light scattering (LLS), video monitoring and a humidity detector to moderate nitrogen flow. The growth occurs under constant temperature conditions via isothermal temperature control. The system may be monitored and controlled by computer.

Figure 4:
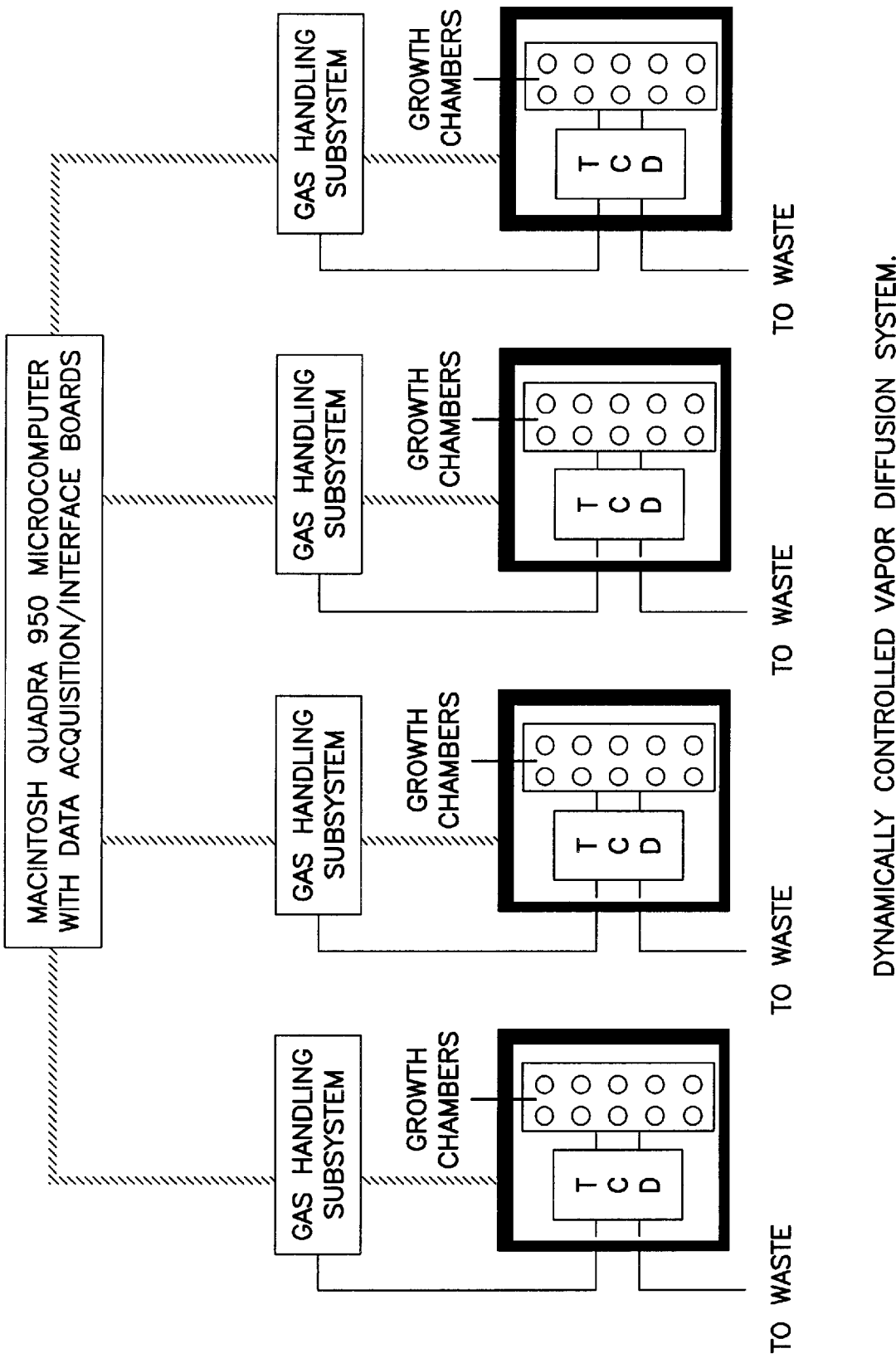
FIG. 4 is a schematic illustration of a dynamically controlled vapor diffusion system.
Figure 5:
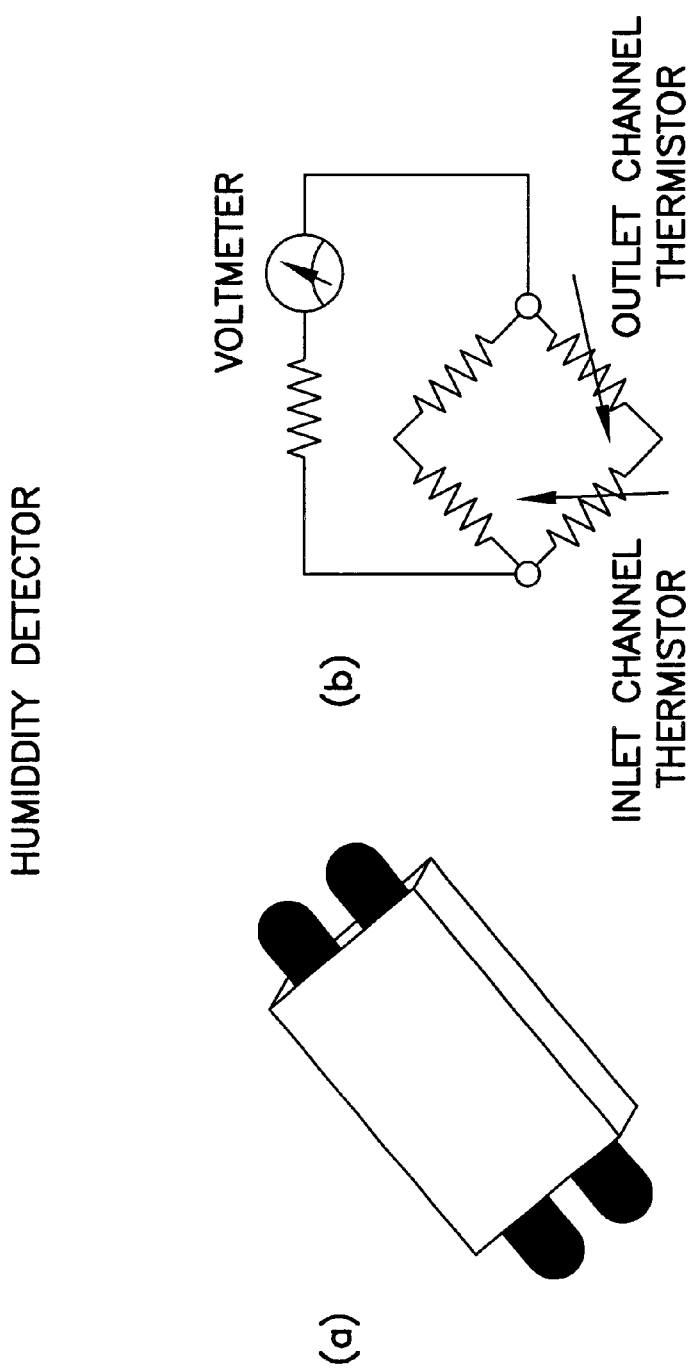
FIGS. 5(a) and (b) show a thermal conductivity humidity detector and its circuit.

Referring now to FIG. 4, the system screens up to 40 different evaporation profiles simultaneously, using growth chambers in which the growth solution is deployed as a hanging drop. Gas flow in and out of each chamber is controlled by a pair of valves (available for example from Lee Company of West Brook Connecticut). The amount of water evaporated from each growth solution at any given time is measured quantitatively using a microvolume thermal conductivity detector (TCD) (available for example from Gow-Mac of Greenbelt Maryland). FIGS. 5 (a) and (b) show a thermal conductivity detector (TCD) used for humidity monitoring and its circuitry.

Figure 6:
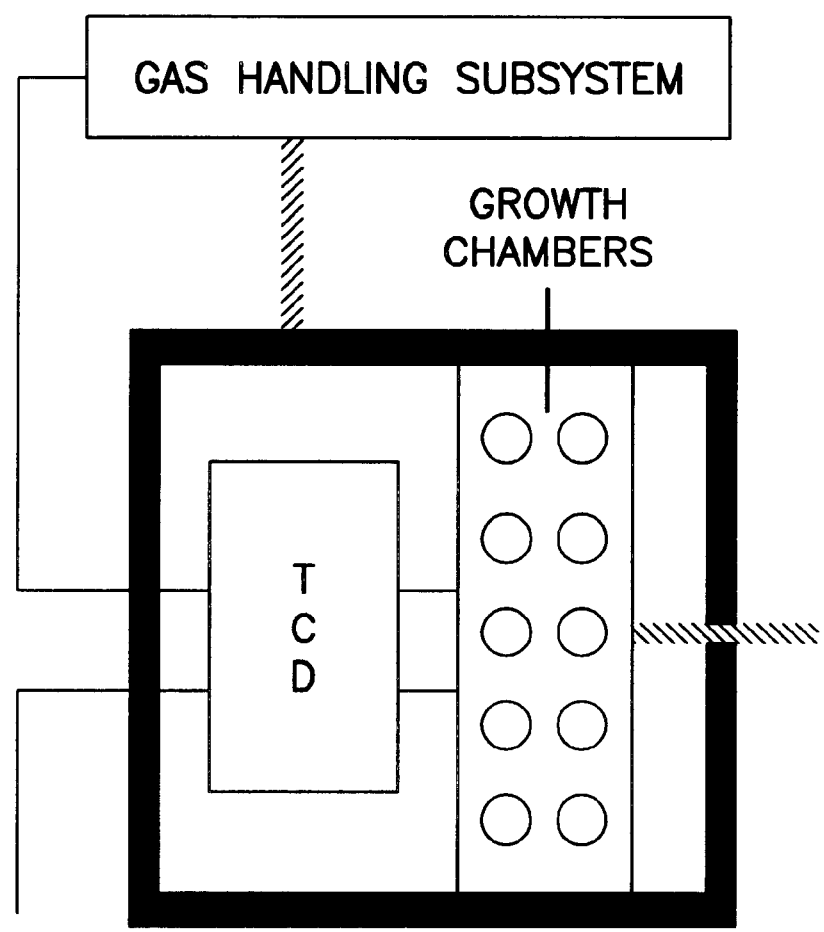
FIG. 6 is an enlarged illustration of one of the elements shown in FIG. 4.
Figure 7:
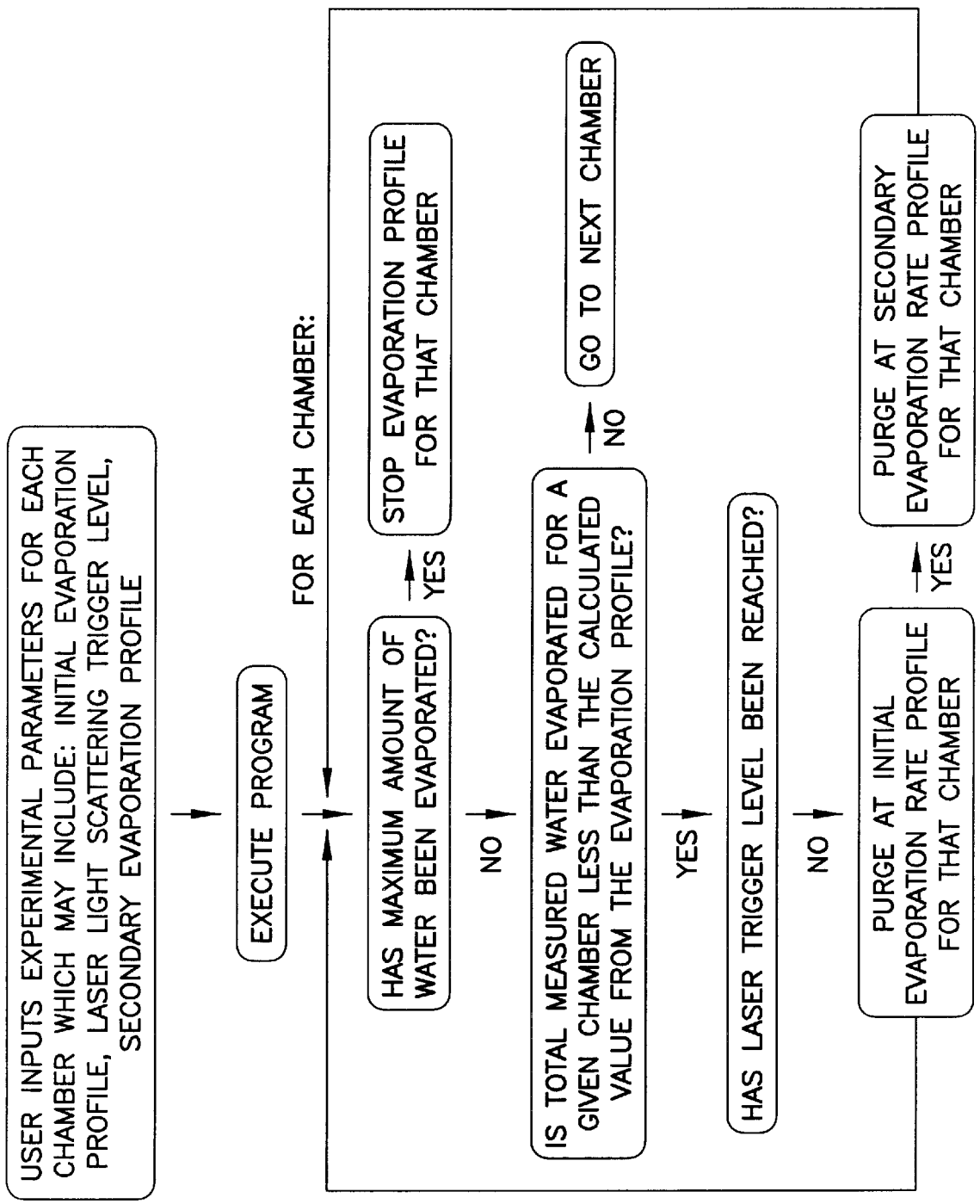
FIG. 7 is a flowchart for software for controlling the vapor diffusion system.

The chambers may be grouped in sets of 10 with each set multiplexed to one TCD. The ten chambers fit onto one baseplate (see FIG. 6), which provides structural support for the chambers, the valves for each chamber, the multiplexing manifolds, and an electrical umbilical. The growth chambers may be controlled and monitored by a microcomputer, for example a Macintosh Quadra 950 microcomputer using custom software written in the program language LabView to monitor each set of 10 growth chambers, allowing for individual or replicate profiles to be executed in any given chamber. Data acquisition and interface boards are used for all analog and digital input/output functions. FIG. 7 provides a flowchart for a software system useful for carrying out the controlling and monitoring functions.

Figure 8:
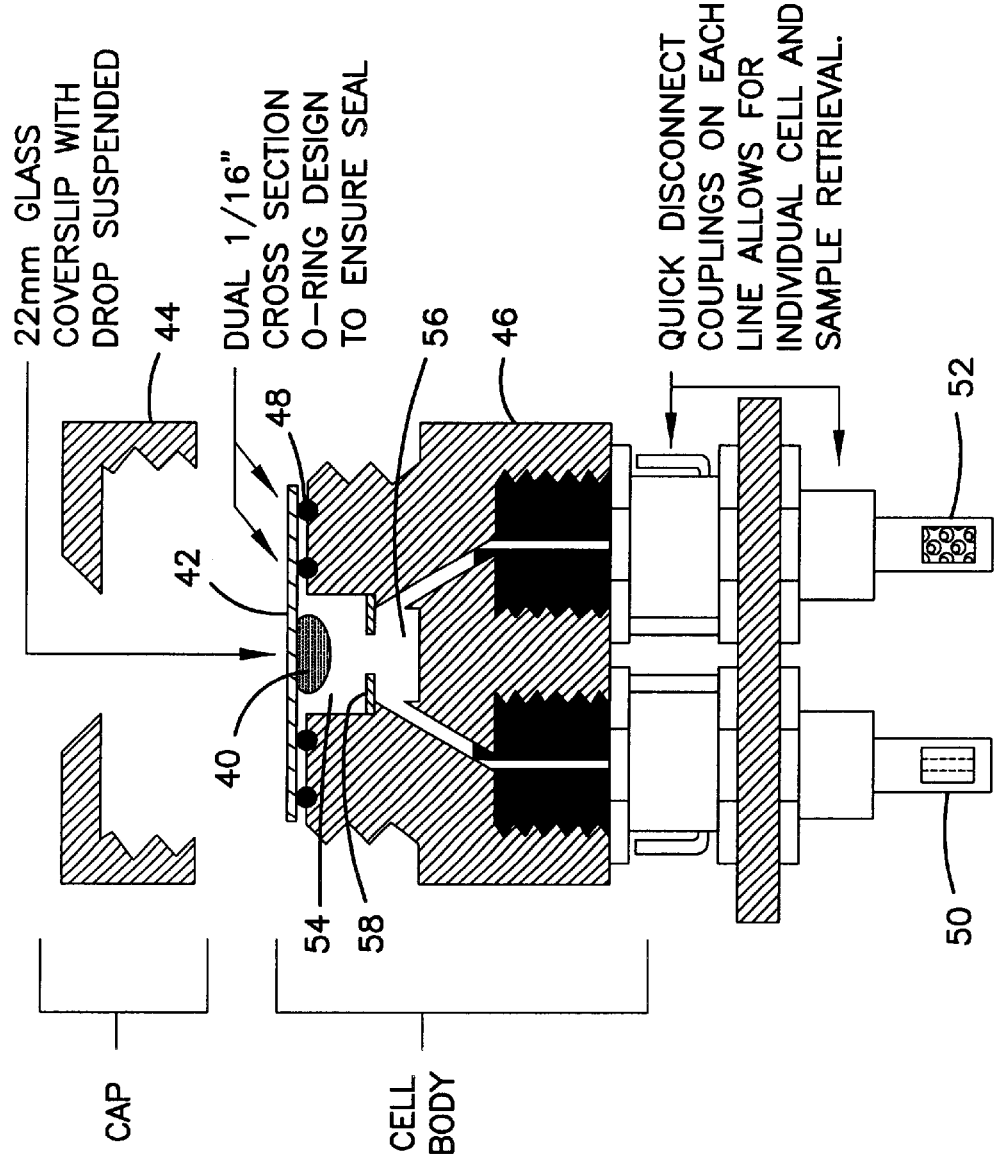
FIG. 8 is a sectional side view of a crystal growth chamber used in the system of FIGS. 4 and 6.

FIG. 8 shows the crystallization chamber. The crystallization chamber is designed to simplify the set up and recovery of experiments and can be made of any suitable material, such as glass, metal or polymeric materials such as acrylic polymers and polysulfone. Materials such as acrylics that are substantially optically transparent are preferred. The growth solution is deployed as a droplet 40 on a standard glass coverslip 42 and placed on the chamber body 46. A threaded cap 44 fits over the coverslip, securing it to the chamber body. Two O-rings 48 (e.g. 1/16 inch in cross section) provide an airtight seal for the chamber when the cap is screwed down finger-tight. The chamber body has two quick-disconnect valves for connection to the purge gas supply and removal lines 50 and 52. This allows removal from the baseplate (e.g., for photography) while maintaining integrity of the airtight seal.

The chamber has dual compartments or sections to aid in controlling evaporation from the drop surface. The first section 54 contains the hanging drop of crystal growth solution and can be considered as the crystallization reaction section. The second section 56 is in communication with the gas supply and removal lines, and solvent evaporating from the growth solution is removed by means of the gas supplied to and removed from the second section 56. The sections 54 and 56 are separated by a barrier 58 that acts to prevent any substantial direct impingement of the gas on the growth solution. However, the barrier permits the passage of evaporated solvent from the first section to the second section. The barrier can be in the form of a washer whose central opening permits vapor to pass to the second section while its body prevents any substantial flow of gas from the second section to the first section. In this case, the washer can be made of metal, plastic or any other suitable material. The barrier can also take the form of a fabric or membrane made of a material or otherwise formed to be permeable to solvent vapor. In this case, the barrier can extend completely between the two sections, without the need for a central opening. When water is the solvent, a polymeric material such as "GORETEX" that permits the passage of water vapor can be used for the fabric or membrane. Other useful materials include a nylon mesh screen material, filter paper or other porous cellulose material, and nucleopore filters. In the case of filter paper, it is preferred that the material be one that does not absorb the evaporated solvent. In the case of the nucleopore filter, the pore size should be sufficiently large to permit passage of the vapor phase molecules to pass therethrough. If the gas flow is permitted to impinge directly on the growth solution, the solvent vapor gradient may become too steep, resulting in the formation of a large number of nucleation sites (a "shower") at the solution surface. This is undesirable since it tends to produce large numbers of small crystals.

A microvolume thermal conductivity detector (TCD) is used to quantitate the amount and rate of water evaporated from each growth solution. The difference in thermal conductivities between dry $N_2$ gas and moist $N_2$ gas produces a signal that can be quantitatively related to the amount of moisture in the purge volume. The integration of this signal with respect to time for sequential purges of a given chamber allows the total water evaporated from each chamber to be determined and provides feedback to the host microcomputer so that virtually any desired evaporation profile may be followed.

A custom software program (e.g. as shown in FIG. 7) written in the graphical programming language LabVIEW (available from National Instruments of Austin, Tex.) running on a Macintosh Quadra 950 (Apple Computer) microcomputer controls all aspects of the system. A user interface allows various experimental control parameters to be entered prior to execution. The program controls the purges of each chamber based upon the evaporation profile entered before execution using feedback from the TCD. This allows virtually any evaporation profile to be followed. The program also performs all data acquisition functions, digital output functions, and writes the cumulative data file to the internal hard disk for subsequent analysis.

EXAMPLE 1

Hen egg white lysozyme was obtained from Calbiochem. NaCl, NaOAc, and glacial acetic acid were obtained from Fisher Scientific. A 50 mM acetate buffer was prepared by dissolving NaOAc in 18 Mohm deionized water. The pH was adjusted to 4.7 using glacial acetic acid. Lysozyme was dissolved in buffer and then dialyzed several times against fresh buffer to remove any salt from the source protein. This solution was then concentrated using Amicon microconcentrators to create a stock solution at 40 mg/mL. A 7% (w/v) stock solution of NaCl was prepared by dissolving the NaCl salt in buffer. All solutions were filtered through 0.22 micron Whatman filters.

Thaumatin, NaK tartrate, and ADA (N-[2-Acetamido]-2-iminodiacetic acid) were obtained from Sigma. Glacial acetic acid was obtained from Fisher Scientific. A 68 mg/mL stock Thaumatin solution was prepared by dissolving the protein in 18 Mohm deionized water. An ADA buffer was prepared by dissolving ADA salt in 18 Mohm deionized water and adjusting the pH to 6.5 with glacial acetic acid. A 0.75M stock solution of NaK tartrate was prepared by dissolving the NaK tartrate salt in ADA buffer solution. All solutions were filtered through 0.22 micron Whatinan filters.

For each protein, lysozyme and thaumatin, the growth solution was deployed onto silanized glass coverslips by mixing 10 microliters of each of the stock protein and crystallizing agent solutions (20 microliters total). Each coverslip was then placed on a chamber and sealed with a screw-down cap. Linear evaporation profiles were performed to determine the effects of evaporation rate on crystal growth results. Solutions were evaporated at 0.041, 0.083, 0.2, 0.34, 0.45, and 1.25 microliters/hr to half the original volume.

Figure 9A:
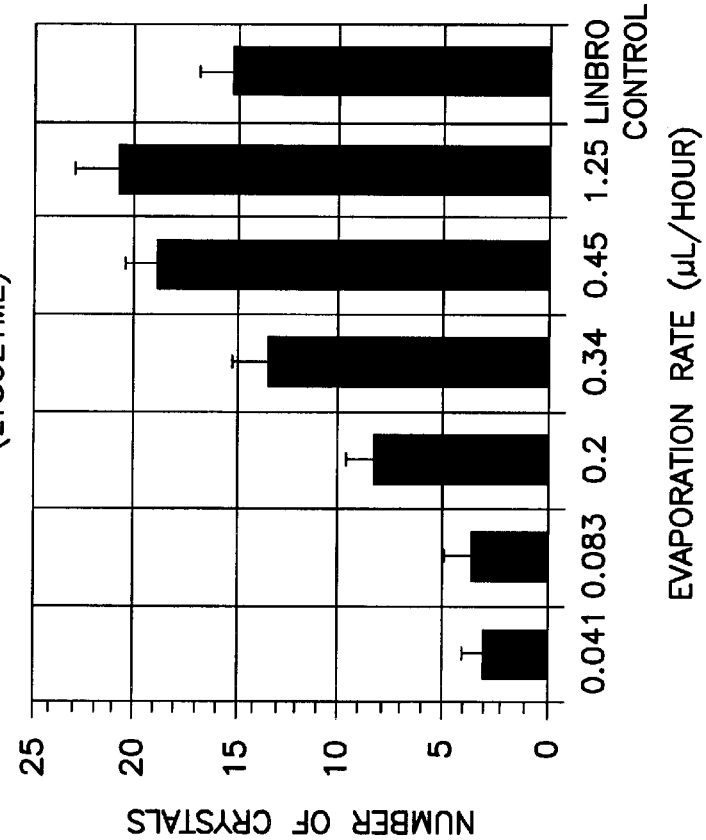
FIGS. 9(a) and (b) show lysozyme crystal growth results at varying evaporation rates.
Figure 9B:
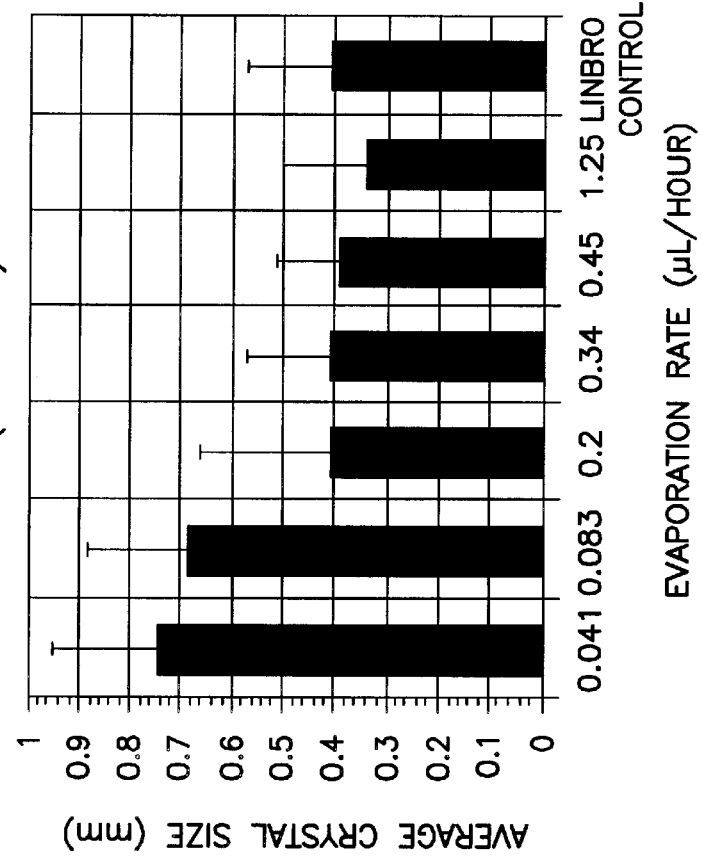
Figure 10A:
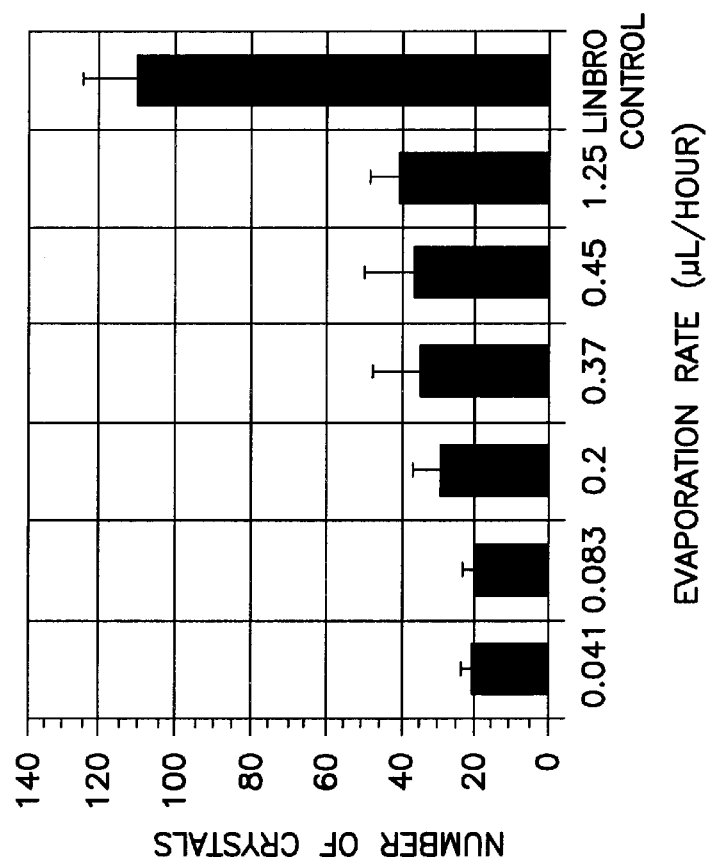
FIGS. 10(a) and (b) show thaumatin crystal growth results at varying evaporation rates.
Figure 10B:
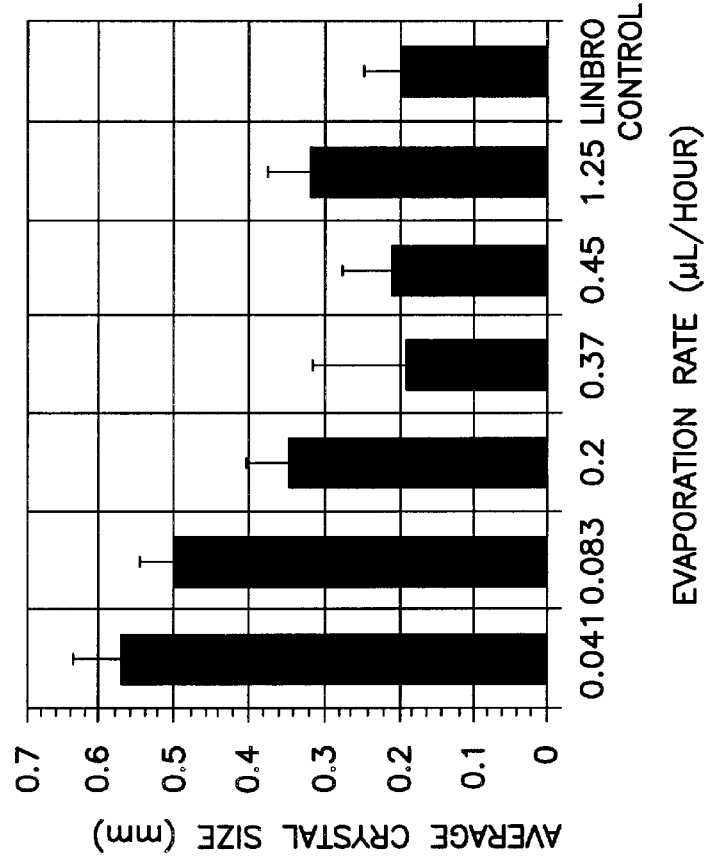

Results from a large number of experiments for the two proteins show that clear, systematic trends are observed as a function of evaporation rate (see FIGS. 9 (*a*) and (*b*) and 10(*a*) and (*b*)). As the evaporation rate is increased, larger populations of smaller crystals are observed. Since the supersaturation level required for nucleation to occur is higher than that needed to sustain crystal growth, the observed results are likely related to the length of time that the solution resides in the nucleation region. For a given evaporation rate, once nucleation occurs, crystal growth can proceed for those nuclei formed. This crystal growth will begin depleting protein from the solution. However, if the supersaturation level is increasing faster due to evaporation than it is decreasing due to crystal growth, then nucleation will continue to occur until crystal growth depletes the protein concentration below the supersaturation level required for nucleation. Hence, faster evaporation rates should maintain a high supersaturation level longer than slower evaporation rates, leading to increased crystal populations. Also, larger crystal populations should generally yield smaller crystals since the amount of protein in the growth solution is fixed and cannot sustain crystal growth to large sizes for a large number of crystals.

Additionally, comparative x-ray analysis of crystals grown using this hardware system with crystals grown by traditional methods have been undertaken. Results from the vapor diffusion/nitrogen systems indicate that longer evaporation profiles generally produce larger crystals and that the larger crystals generally produce enhanced x-ray diffraction.

Also, crystals of equal size grown at different evaporation rates show a wide and overlapping variation of diffraction characteristics (signal to noise, resolution).

Figure 11:
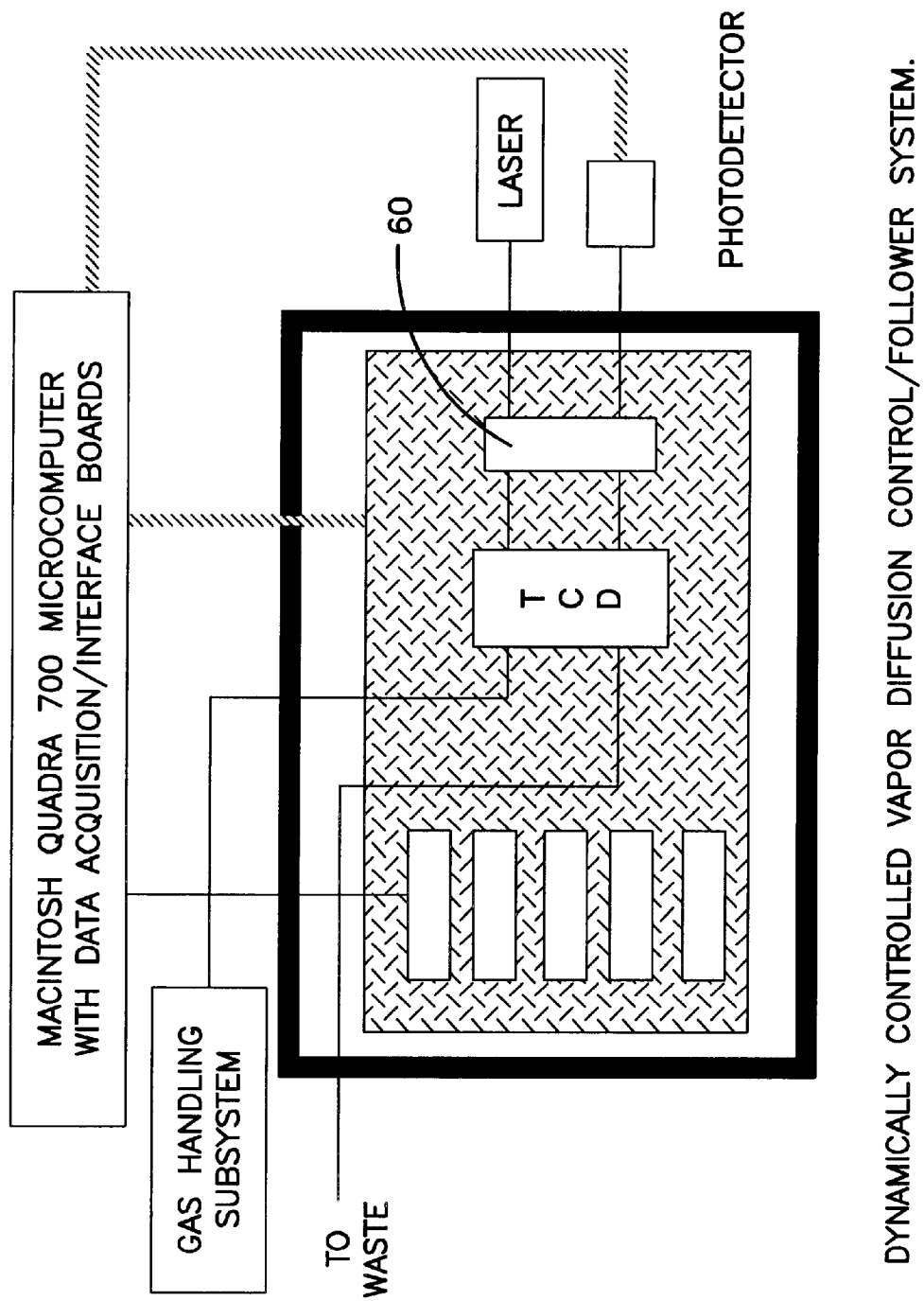
FIG. 11 illustrates an example of a dynamically controlled vapor diffusion control/follower system.

In a second aspect, the present invention can utilize a control/follower system to monitor and control a number of dynamically controlled vapor diffusion crystallization chambers (the follower chambers) by means of the information collected for a single chamber (the control chamber). A dynamic controlled vapor diffusion control/follower system (DCVDC/FS) (see FIG. 11) has been constructed that provides dynamic control of the supersaturation level during the crystal growth process. This device uses concepts similar to the previously described system that controls supersaturation levels. The DCVDC/FS system also incorporates a laser light scattering (LLS) subsystem as a noninvasive probe for detecting aggregation events occurring in a growth solution. The detection sensor provides feedback to the controlling microcomputer so that the evaporation profile can be modified in real time in an attempt to optimize crystal growth. The illustrated system has six growth chambers arranged in a control/follower configuration with the control chamber 60 containing the LLS system which is connected to the humidity sensor (e.g. a TCD). Some or all of the remaining chambers are evaporated at a rate that mimics that of the control chamber.

Figure 12:
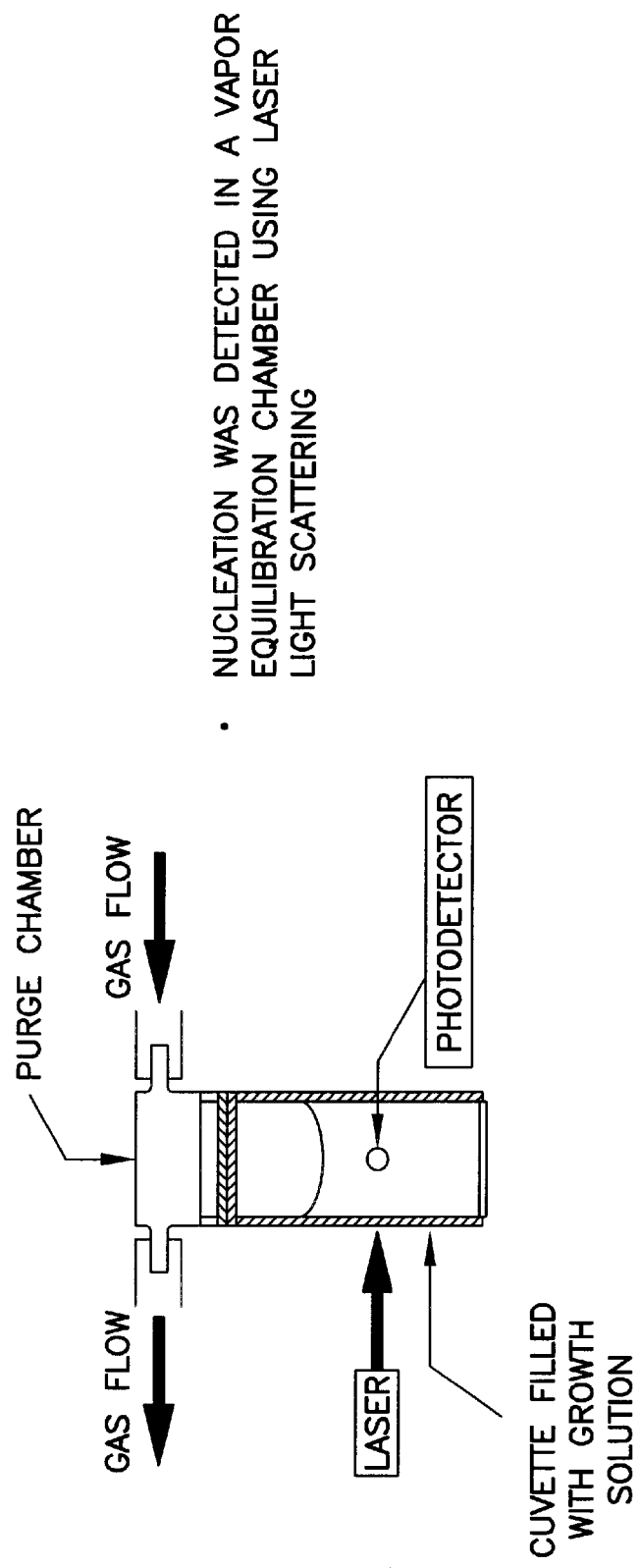
FIG. 12 illustrates a further example of a crystal growth chamber.

Each of the six growth chambers contain the following components: cuvette, upper glass purge chamber, three piece aluminum housing, and thumbscrew. The control chamber (see FIG. 12) also contains two fiber optic cables, one for the 5 mW, 633 nm He—Ne laser (available from Melles Griot of Irvine, Calif.) and photodetector (available from Hammamatsu of Bridgewater, N.J.). In the aluminum housing, the top component is milled out to accomodate the upper chamber cell and gas flow lines. Additionally, a threaded portal is provided through which a thumbscrew any be deployed against the upper chamber cell to sealit against the cuvette. A cylindrical portal may be milled through the thumbscrew to provide access for visual observation. The middle component of the aluminum housing is milled through to provide a pathway for the cuvette mid upper-chamber to meet when sealed against each other. This component essentially acts as a removable spacer to allow the cuvette to be removed easily from the lower component. The lower component is milled to accept the cuvette. It also has portals milled out for two fiber optic cables. A portal through the bottom of the lower component is provided to allow for visual observation. Typically, a light source will provide backlight through the bottom of the lower component.

The growth chamber is a commercially available glass fluorimeter cuvette. The portion of the cell where the actual growth solution is contained has a cross sectional dimension of 2 mm×10 mm and is 12.5 mm high. A second chamber is sealed on the top of the cuvette to aid in controlling the evaporation of water from the growth solution. The two chambers are spearated by a barrier that is permeable to solvent vapor and substantially prevents any direct impingement of the purge gas on the growth solution as in the previous embodiment. Transmission and detection of the laser light is accomplished via optical fibers. The entire assembly resides in a three component aluminum housing which provides mechanical support for the upper chamber cell and the laser and photo detector fiber optic cables. The aluminum housing also provides a mechanism for sealing the upper chamber to the growth cell (via a thumb screw).

EXAMPLE 2

Hen egg white Lysozyme was obtained from Calbiochem. NaCl, NaOAc, and glacial acetic acid were obtained from Fisher Scientific. A 50 mM acetate buffer was prepared by dissolving NaOAc in 18 Mohm deionized water. The pH was adjusted to 4.7 using glacial acetic acid. Lysozyme was dissolved in buffer and then dialyzed several times against fresh buffer to remove any salt from the source protein. This solution was then concentrated using Amicon microconcentrators to create a stock solution at 45 mg/mL. A 7% (w/v) stock solution of NaCl was prepared by dissolving the salt in buffer. Equal volumes of the stock protein and NaCl solutions were mixed and passed through a filter loop to produce a solution clean enough to use for laser light scattering. This loop consisted of a peristaltic pump, tubing, and a 0.22 micron Whatman filter. The solution was filtered for 30 minutes and then deployed directly into the cuvettes.

Figure 13:
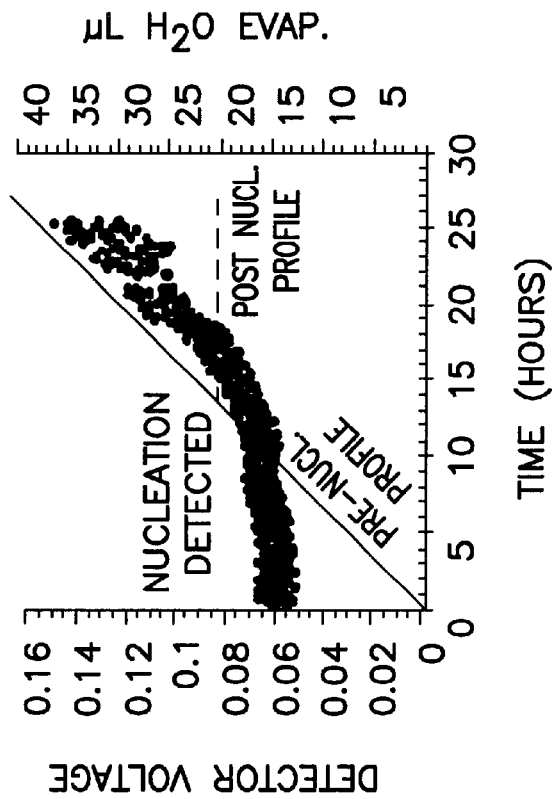
FIG. 13 shows evaporation profiles overlaying typical static laser light scattering signal as aggregation occurs.

200 microliters of the growth solution is deployed in the cuvette, inserted into the chamber assembly and sealed. Initial experiments with this device have revolved around the use of linear evaporation profiles in the early stages of the experiment. Once nucleation is detected by the light scattering system, the profile is modified for half of the chambers, with the original profile continued for the remainder. This allows a direct comparison between the results obtained from continued evaporation at the original linear rate versus modification of that rate in response to the light scattering sensor. Two different evaporation rates in the early stages of the experiments were investigated. The growth solutions were evaporated at 0.83 and 1.389 microliters/hr., respectively, until the laser light scattering sensor was triggered at the detection of nucleation. At this point, half of the chambers ceased evaporation while half continued at the original evaporation rate (to half the original volume). There is a distinct change in the slope of the photodetector response as aggregation occurs. This change is subsequently responded to by the computer system that controls the evaporation profile. Typical experimental profiles and a typical response of the photodetector to aggregation are shown in FIG. 13. There is a distinct change in the slope of the photodetector response as aggregation occurs. This change is subsequently responded to by the computer system that controls the evaporation profile.

Figure 14:
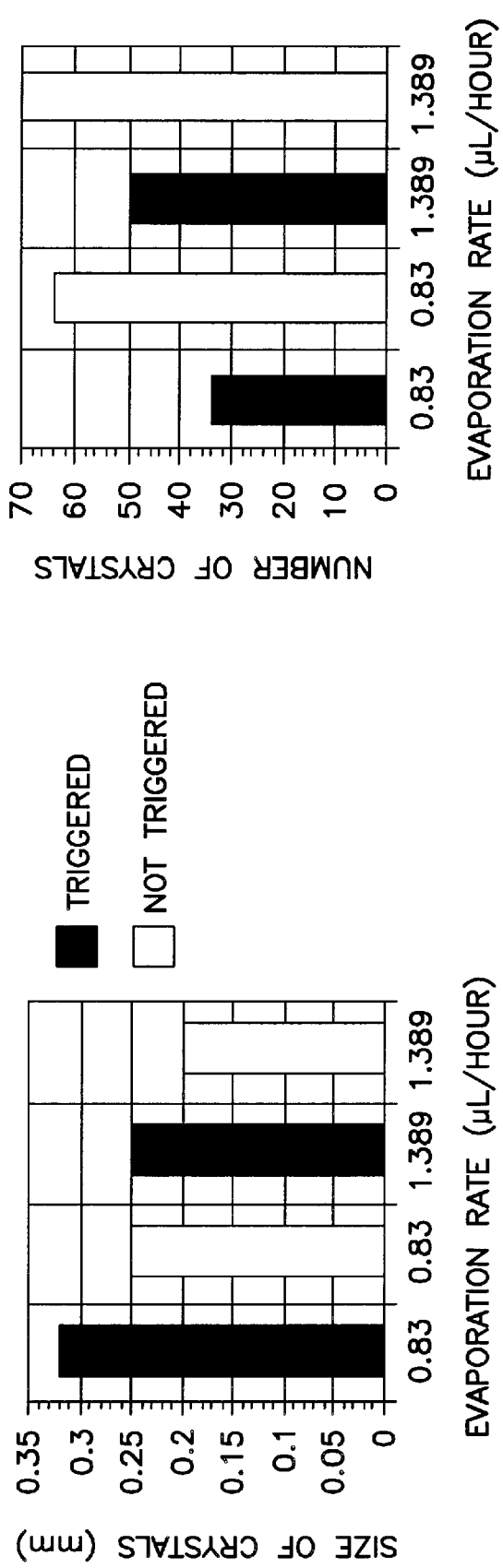
FIG. 14 shows results for lysozyme crystal growth at different evaporation rates, under conditions where the evaporation was terminated upon detection of aggregation and/or nucleation (triggered) and where evaporation continued after the onset of nucleation (non-triggered).

Preliminary results for this system indicate that modification of the evaporation profile in response to light scattering detection of nucleation yields improved crystallization results. Generally, modification of the evaporation profile after nucleation detection, in this case a reduction in evaporation rate, results in a smaller population of slightly larger crystals. A faster initial rate of evaporation also affects the crystal growth results, yielding a larger population of smaller crystals than observed at the slower initial evaporation rate (FIG. 14). As explained earlier, it is likely that growth solutions in which nucleation is detected and evaporation ceased have fewer nuclei, allowing the remaining protein in solution to "feed" growth of these crystals to a larger size. The growth solutions that continue evaporating likely reside in a nucleation region longer, producing more crystals which cannot grow as large.

Temperature Based Systems

The present invention also can be used as a dynamic control system that controls the supersaturation state of materials to be crystallized from solution via precise temperature changes. Temperature can be precisely controlled and used as a tool to control the population and size of the crystals being obtained, e.g. protein crystals. It also is possible to use a non-invasive sensor to detect aggregation events and modify the temperature program for a given experiment in response to the sensed events. This aspect of the present invention also is useful for the control/follower concept. This again is accomplished by monitoring aggregation events in the control chamber and controlling the temperature of the follower chambers in response to the behavior of the experiment in the control chamber. In general, the temperature of the growth solution will be lowered or raised (depending upon whether the substance in question shows decreased solubility with lower temperature or higher temperature) until nucleation is initiated. At this point, the temperature change can be stopped or reversed to inhibit further nucleation that could hinder the growth of larger crystals. In some cases, it will be desirable to reverse the temperature change and then hold the solution at a constant temperature when it reaches a desirable temperature for crystal growth.

Figure 15:
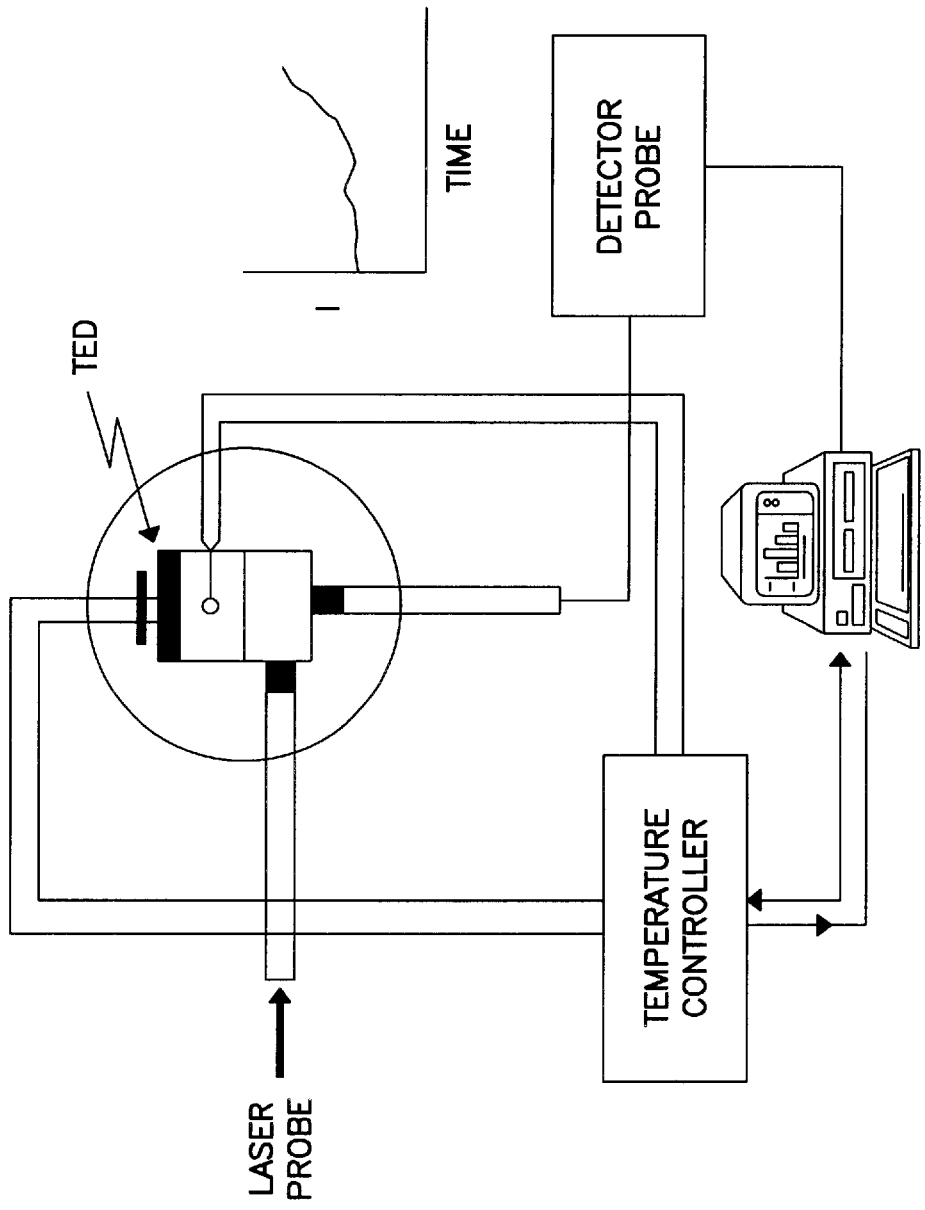
FIG. 15 is a block diagram of a system for dynamic control protein crystal growth (DC/PCG) via temperature induction.
Figure 16:
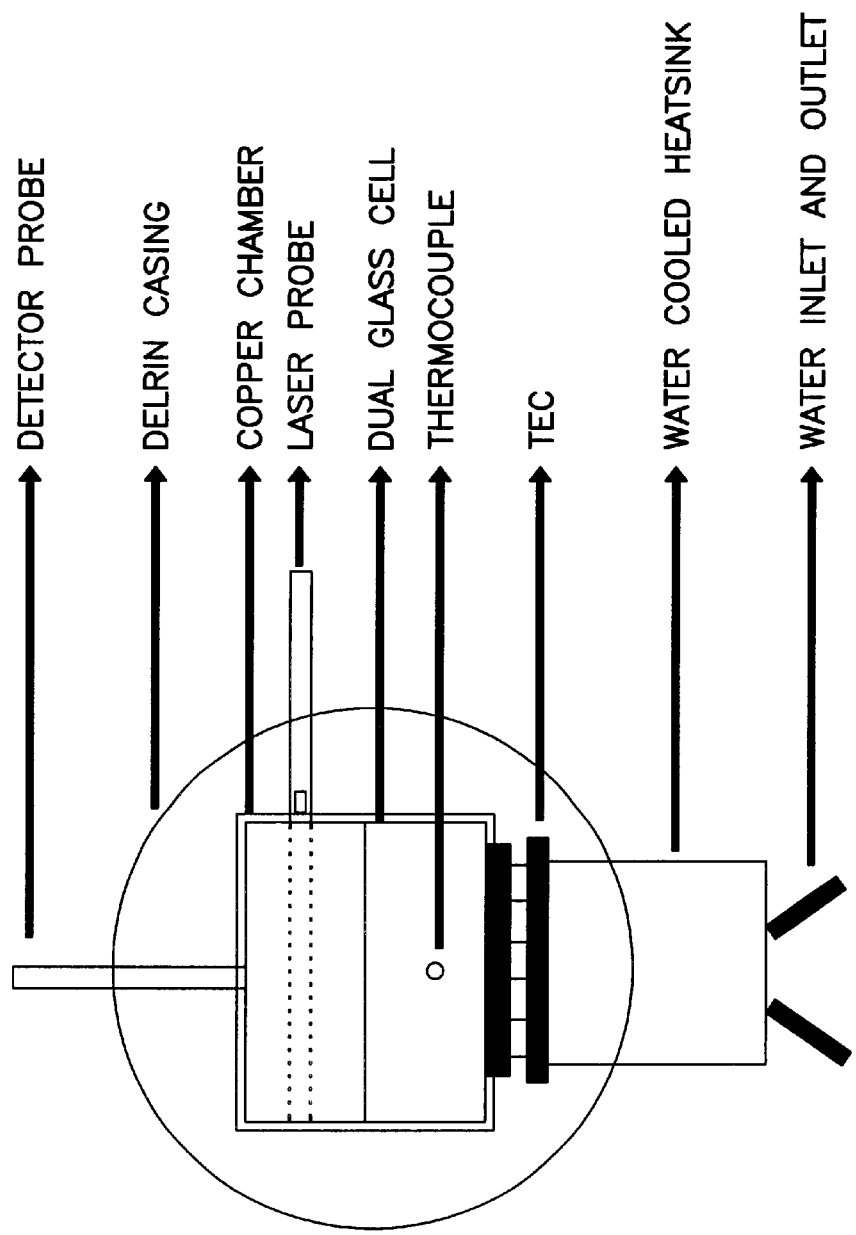
FIG. 16 is an enlarged view of a growth chamber from the system of FIG. 14.

FIG. 15 is a block diagram of an example of a system for protein crystal growth effected by temperature change. This diagram outlines the major components for dynamically controlled temperature system (DCTS). The sample chamber in the center circle is instrumented with a thermal electric device (TED) for temperature change and control and with laser light scattering via laser probe and detector probe. The system is monitored and controlled via computer. In this example, the growth chamber has two compartments, with a laser probe being centered in one of the chambers. FIG. 16 is an expanded view of the growth system depicted in FIG. 15.

Figure 17:
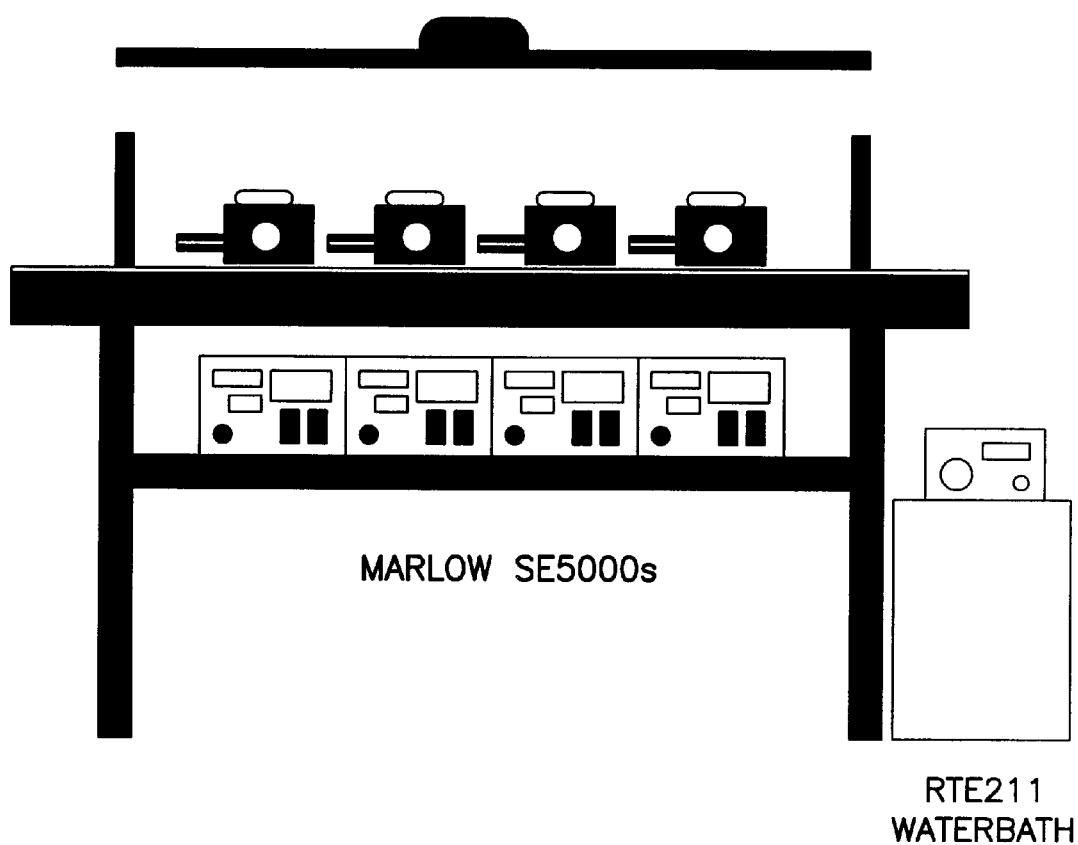
FIG. 17 is a scematic illustration of a dynamically controlled temperature system.

As shown in FIG. 17, this system uses precise temperature adjustments to initiate, monitor, and control the growth of protein crystals. Temperature is manipulated via miniature thermoelectric devices (TEDs) under computer control to change the temperature in virtually any desired manner. Detection of aggregation events is accomplished using a static laser light scattering system (LLS), which acts as a sensor to provide feedback to the controlling microcomputer. All aspects of the systems are monitored and adjusted by a 486 microcomputer containing a data acquisition interface card. Custom software written in QuickBASIC allows the user to set a particular temperature program for a given experiment.

Figure 18:
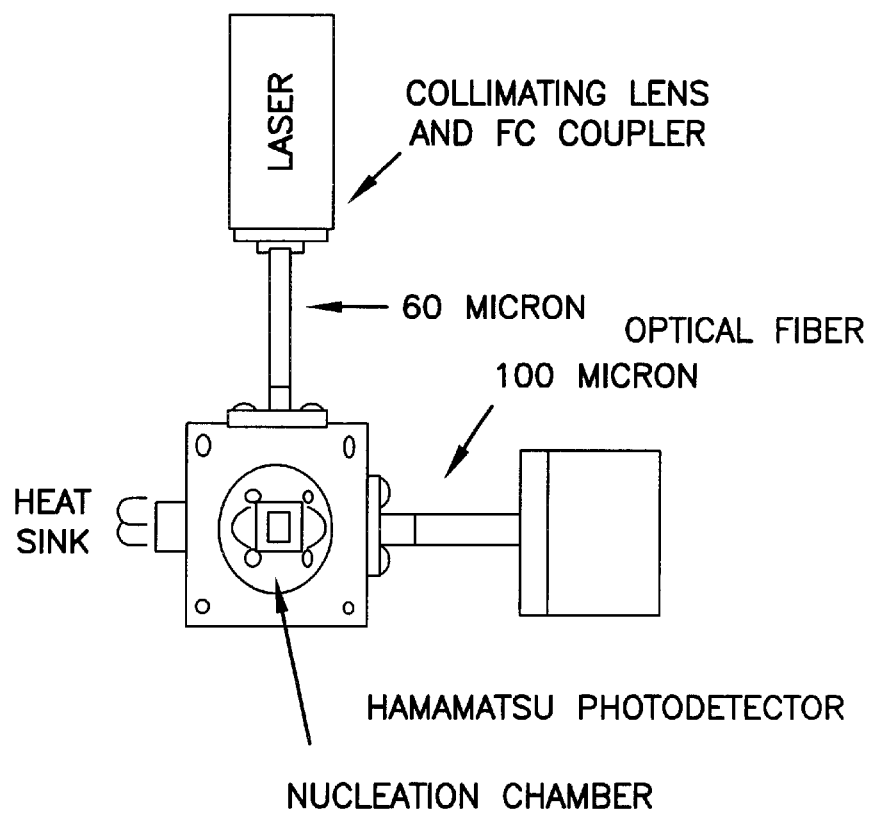
FIG. 18 is a schematic illustration of laser light scattering with nucleation chamber.
Figure 19:
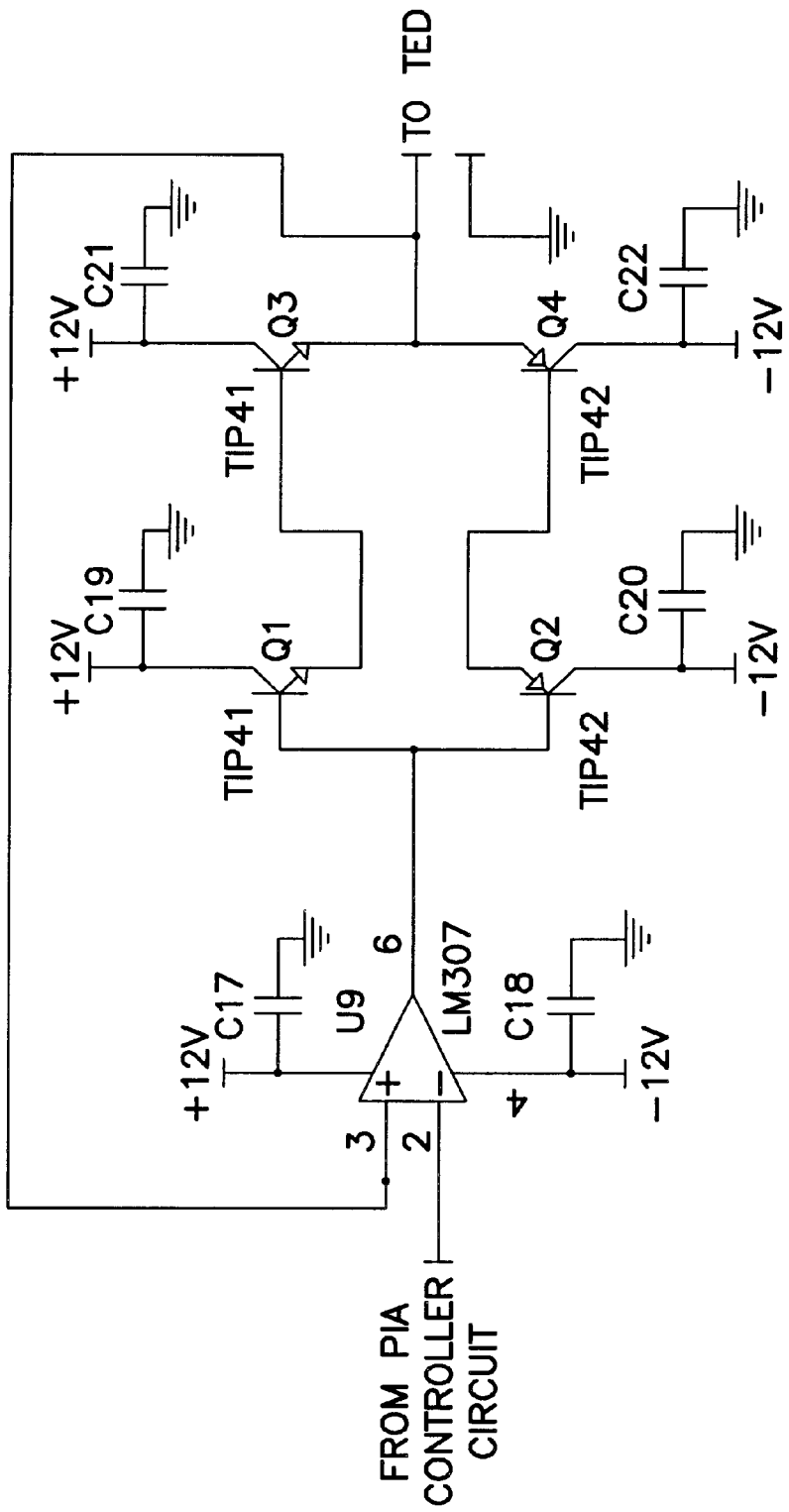
FIG. 19 is circuit diagram for a temperature controller that can be used with the controlled temperature system.

An example of the DCTS apparatus is shown schematically in FIG. 18. The copper jacketed nucleation chamber houses a 10 mm glass cuvette (Starna Cells, Inc., Atascadero, Calif.) which contains 200 microliters of the appropriate growth medium. Generally, a volume of at least 50 micorliters is needed since it can be difficult to couple the laser into a smaller volume. The use of a container for the growth solution permits better thermal contact and resultant improvement in temperature control for the solution. The copper-jacketed nucleation chamber is surrounded by Teflon encased in an aluminum block. The nucleation chamber, in conjunction with a Marlow 5000 series temperature controller (available from Marlow Industries, Dallas, Tex.), an IBM compatible PC, thermoelectric device, and type T thermocouple, allow precise temperature control of the protein growth medium. The static laser light scattering geometry is also shown. Laser light from a helium-neon 633 nm, 5 mW Melles Griot laser is directed into the protein solution via a fiber optic cable. A second fiber optic cable is placed at 90° to the incident laser fiber and collects scattered light that is carried to a photodetector. The output of the photodetector is returned to the controlling CPU in the form of an analog signal. The controlling CPU compares voltages and modifies temperatures as defined by the experimental parameters. The nominal error for temperature control associated with this experimental set up is ±0.1° C. with a maximum error of ±0.25° C. A circuit diagram of a particularly useful temperature control system is shown in FIG. 19.

The growth solution is deployed into a cuvette, which is then placed in the copper jacket and sealed with a cover. Temperature is controlled using a small TED powered by a commercial TED controller/power supply (Marlow Industries) under the direction of a microcomputer. Custom software allows user defined temperature programs to be executed and modified in response to the LLS signal. A flowchart for the software system is shown in FIG. 20.

Figure 20:
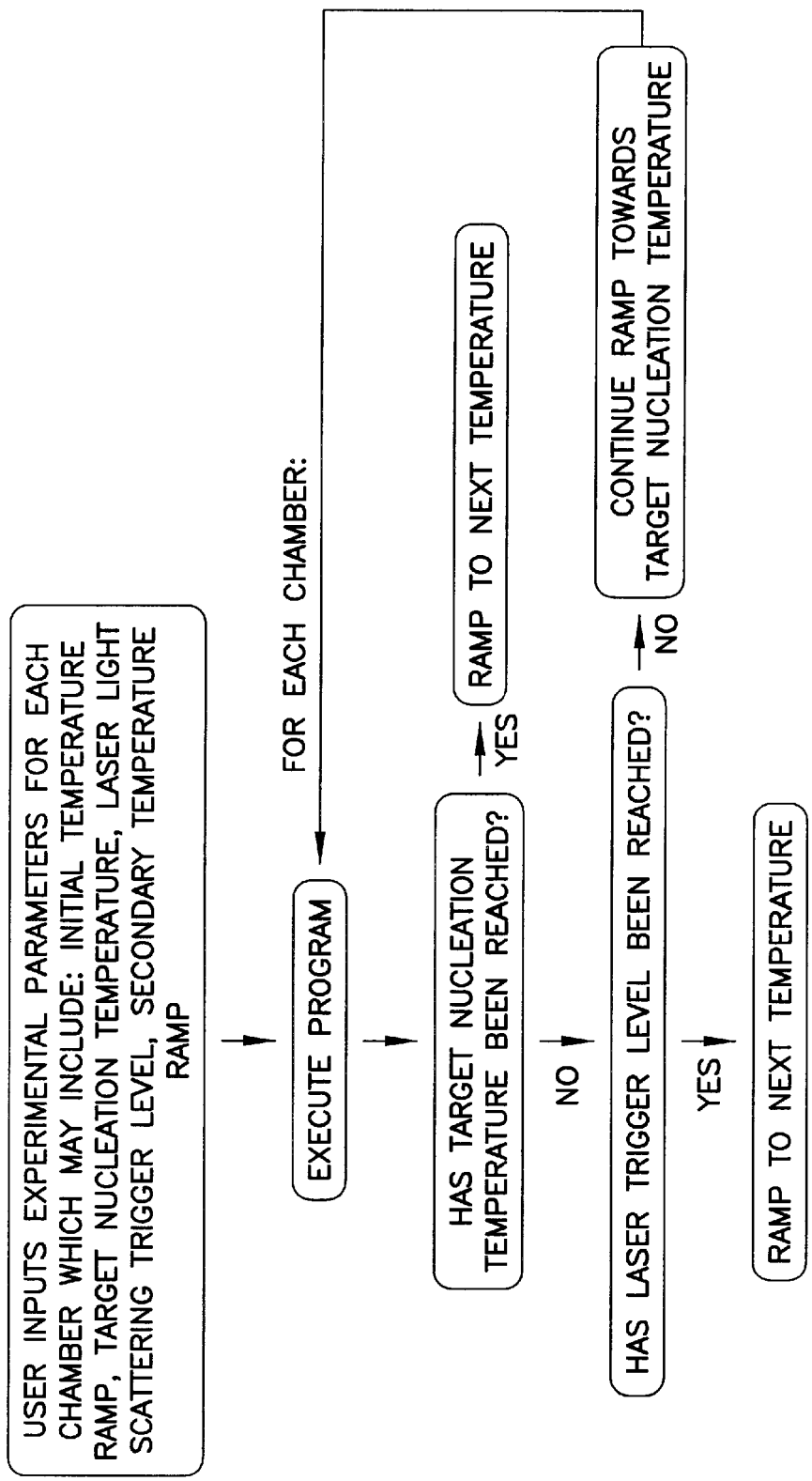
FIG. 20 is a flowchart for software for controlling the controlled temperature system.
Figure 21:
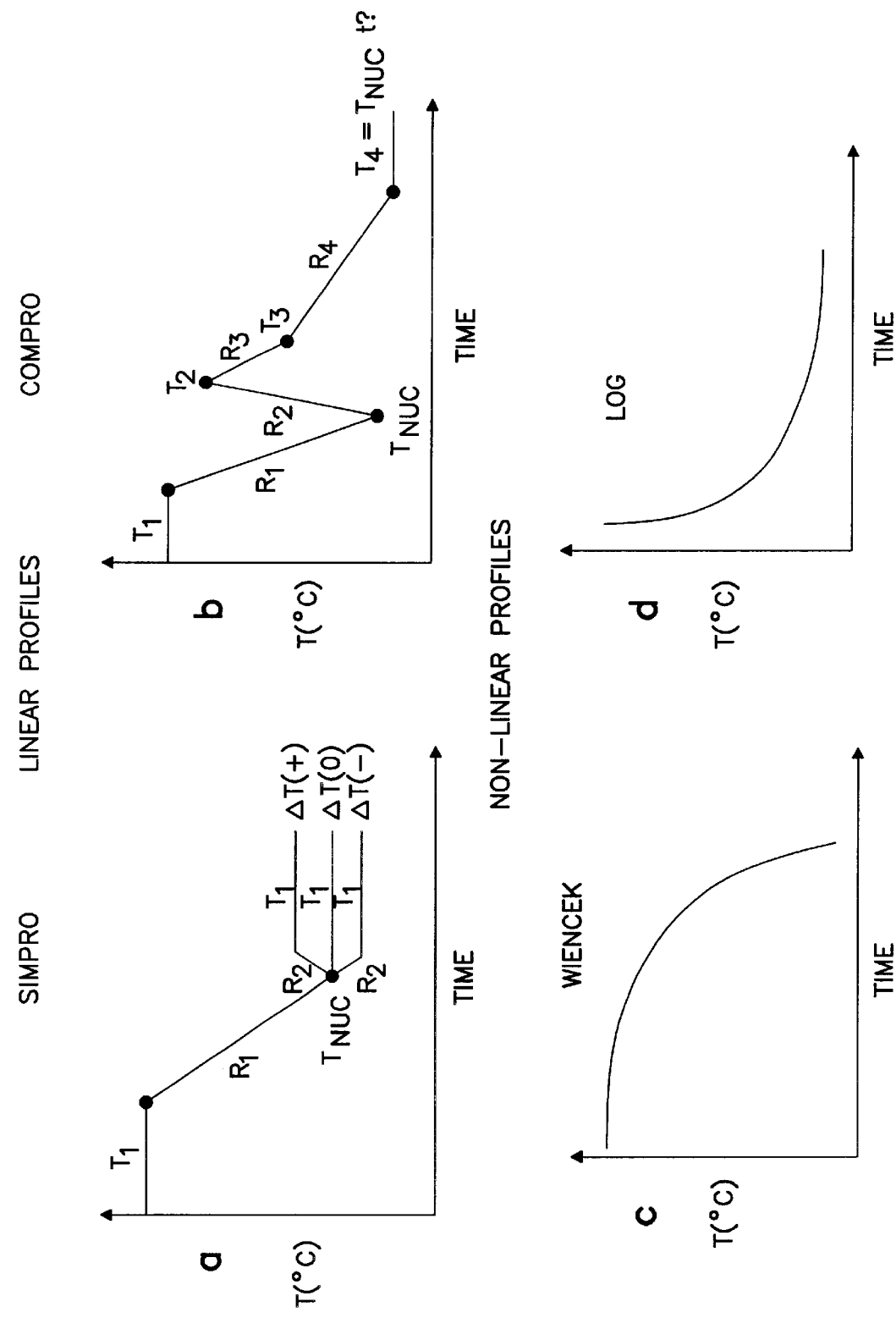
FIGS. 21(a)–(d) show examples of computer generated temperature profiles useful with the temperature induction protein crystal growth systems.
Figure 23A:
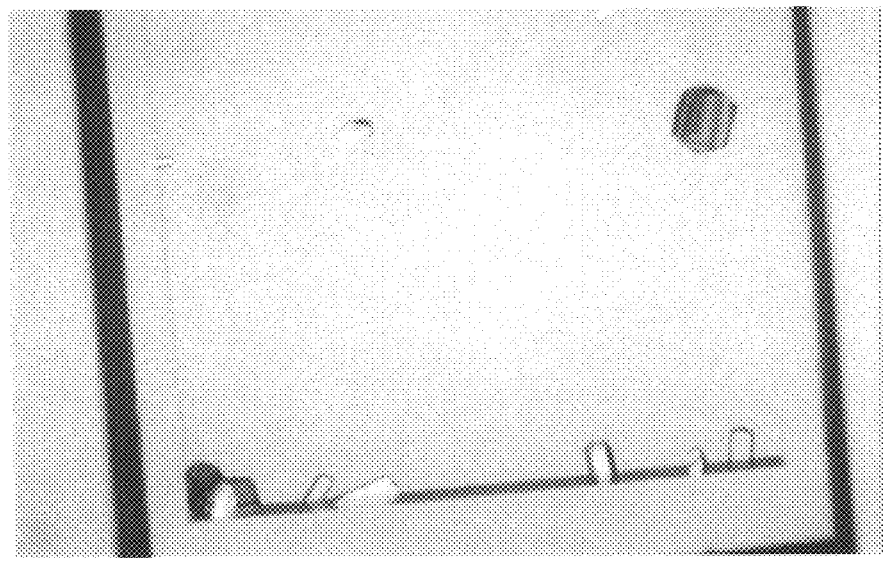
FIGS. 23(a)–(d) are micrographs showing lysozyme crystals obtained from experiments whose results are graphed in FIGS. 22(a)–(d).
Figure 23B:
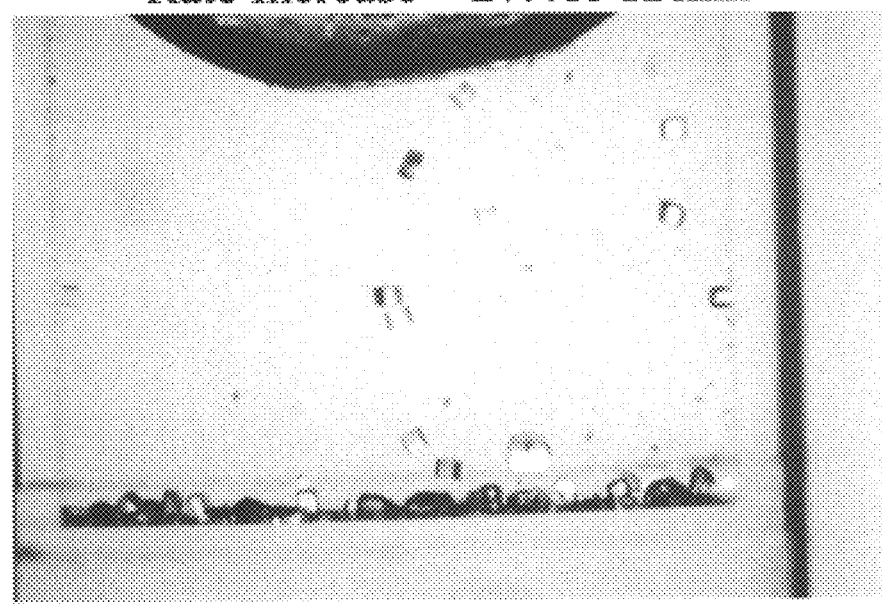
Figure 23C:
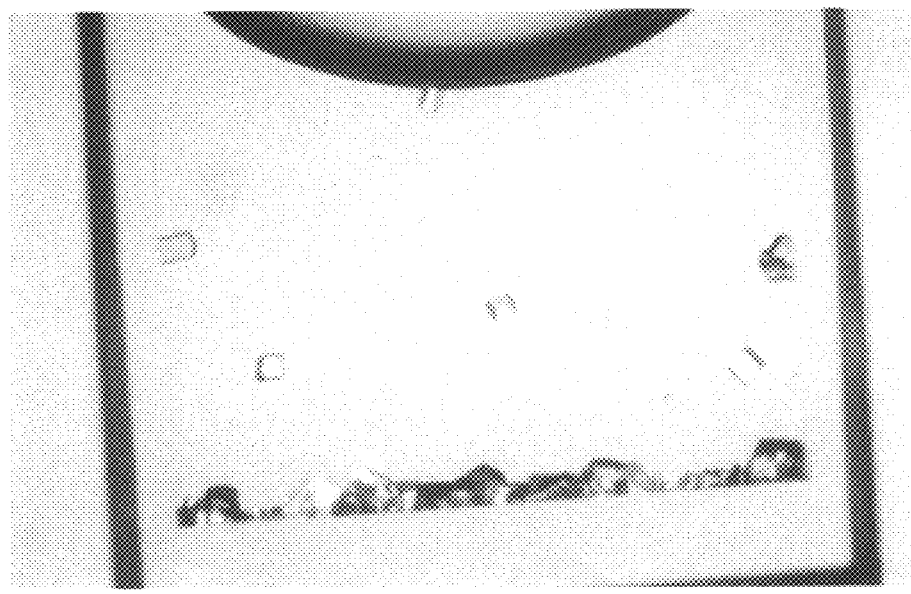
Figure 23D:
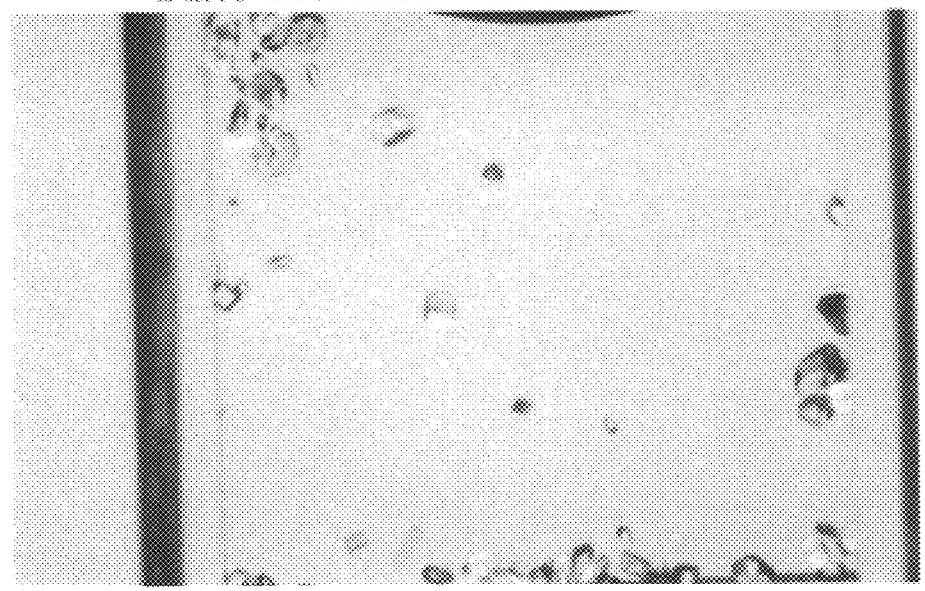

A custom software program (e.g. as shown in FIG. 20) written in QuickBasic running on a 486 microcomputer is used to control all aspects of the system. For a particular experiment, this program allows the user to enter the pre-nucleation temperature profile, the photodetector signal level which designates that aggregation events are occurring, and the postnucleation temperature profile. The programs can control the temperature profile for the reaction in any desired manner. For example, one can allow very simple temperature profiles to be executed (SIMPRO) while the another allows much more complex temperature profiles to be executed (COMPRO) in an attempt to optimize crystal growth. Examples of thermal profiles that can be used for temperature induction of protein crystal growth are shown in FIG. 21. These profiles are generated by the thermal control computer software developed in house. Simple straight forward profiles (Simpro) and complex profiles (Compro) can be designed with the software. The software/microcomputer perform all control and data acquisition functions, recording the data files to an internal hard disk.

The temperature based system can be applied to any material to be crystallized. It is believed to be particularly useful for macromolecular materials such as proteins, nucleic acids and virus particles, especially proteins. In addition, it should be recognized that the proteins that will be most suitable for temperature controlled crystallization are those that show a $\Delta B_{22}/\Delta T$ value of at least $2\times10^{-5}$ mol ml/g$^2$ deg, where B is the osmotic second virial coefficient, a measure of protein-protein specific interactions in a specific solution condition. Examples include lysozyme, hen eg albumin, pepsin, alpha-chymotrysinogen A, equine serum albumin, bovine serum albumin, thaumatin, neurophysin-dipeptide complex, bovine insulin (T3R3), edestin, porcine insulin (T3R3) and human insulin-4-hydroxybenzamide.

EXAMPLE 3

Chicken egg white lysozyme was obtained from Calbiochem. Bovine insulin (pancreas), and porcine insulin (pancreas) were obtained from Sigma. All proteins were used as received without further purification. Zinc acetate dihydrate was obtained from Sigma Chemical Company. Acetone, trisodium citrate sodium acetate trihydrate, and sodium chloride (all certified, ACS reagent grade) were obtained from Fisher Scientific. Lysozyme was crystallized using solubility data collected by Cacioppo and Pusey. The crystallizing medium consisted of 25 mg/mL of lysozyme and 2.5% sodium chloride in 50 mM sodium acetate buffer at pH=4.4. Both bovine and porcine insulins were crystallized from 0.05M trisodium citrate and 0.0075M zinc acetate in the presence of 0.75M sodium chloride, 15% acetone, and 5% water at pH=6.4 (M. M. Harding, et al. (1966) J. Mol. Biol. 16, 30:323–327). All growth media were centrifuged and filtered prior to use.

Temperature-induced bulk crystallization was accomplished by incubating the crystallizing medium at an initial temperature at which the protein is in a quasi-equilibrium state. At this temperature, aggregate size distribution is stable and stable baseline voltages are obtained. After steady state data were accumulated, temperature was decreased at programmed rates to increase the level of supersaturation and affect protein aggregation. The aggregation event was defined as a percentage above steady state voltage. After aggregation was observed, the temperature was increased at programmed rates to a final growth temperature.

The present system successfully used static laser light scattering to detect the aggregation of lysozyme and effectively to decouple the nucleation and growth phases of lysozyme crystal growth. This was accomplished by inducing nucleation at low temperature/high supersaturation conditions, observing an increase in the total intensity of the scattered light as measured by SLS, and increasing the temperature to dissociate some of the aggregates and provide for a better environment for the growth of remaining aggregates. The change in scattering voltage with respect to temperature changes is shown in the double Y graphs of FIG. 22. These graphs depict detector voltage and temperature versus experiment time. These representative plots all show that scattering voltage (particle size) increases with decreasing temperature (protein aggregation) and that the onset of voltage increase is directly correlated with the decrease in temperature. As the temperature is increased, particle size decreases (aggregates dissociate) and the decrease in the magnitude of the scattering voltage is correlated with the onset of the temperature increase. Crystal populations and morphologies obtained from the experiments described in FIG. 22 are shown in the micrographs of FIG. 23.

These photomicrographs clearly demonstrate that aggregation at a low temperature/high supersaturation condition followed by an increase in temperature to an environment of lower protein supersaturation affects the population of microscopic crystals produced. Approaches to both the nucleation temperature (the temperature where aggregation first occurs) and the final growth temperature affect both the number of microcrystals produced at the nucleation temperature and the number of microcrystals that are dissociated when the temperature is increased. Porcine and bovine insulins were also crystallized by DC/PCGT. Static light scattering data demonstrates that insulin aggregates rapidly with decreasing temperature and that the particle size distribution could be reversed with an increase in temperature. This is shown in FIG. 24(a)–(d). Small populations of insulin crystals ranging in size from 0.2 to 0.4 mm were produced. Details of the experimental conditions are presented below.

Figure 24B:
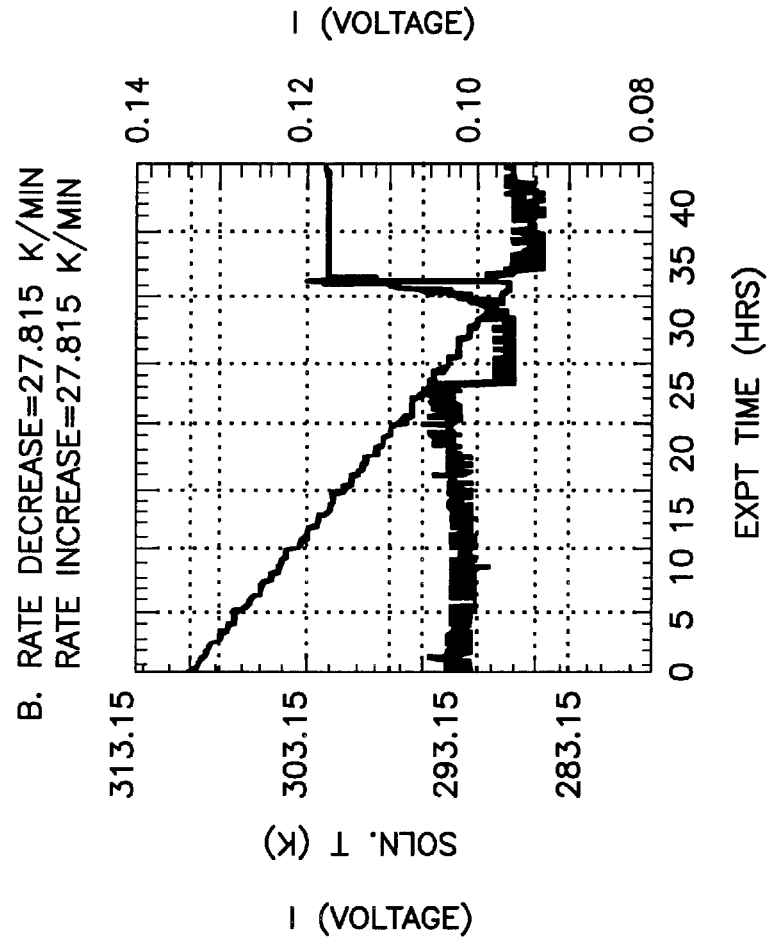
FIGS. 24(a) and (b) show plots of voltage and solution temperature versus .experiment time for bovine insulin aggregates and/or nuclei.
FIGS. 24(c) and (d) show plots of voltage and solution temperature versus experiment time for porcine insulin aggregates and/or nuclei.
Figure 24A:
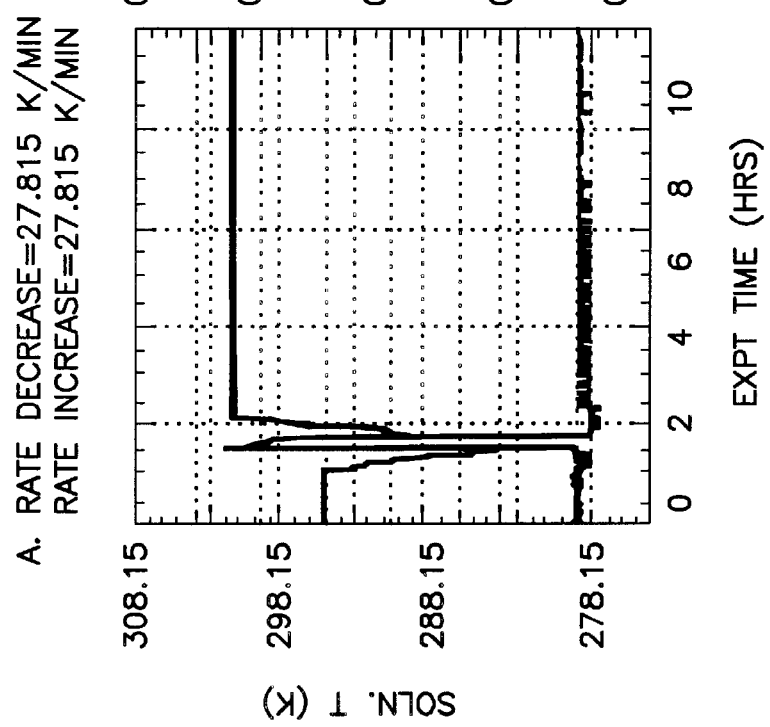

With reference to FIG. 24(a), Bovine insulin (Sigma, 10 mg) was dissolved in 1.5 mL of 0.02M HCl. The following reagents were added in the order listed: 150 microliters of 0.15M zinc acetate, 750 microliters of 0.2M trisodium citrate, 510 microliters of acetone, 90 microliters of water, and 0.18 g of sodium chloride. The pH was increased to about 11 with microliter volumes of dilute sodium hydroxide to solubilize all medium components and then was backtitrated to 6.4 with microliter amounts of dilute hydrochloric acid. The medium was heated at 40° C. for several minutes and then centrifuged at room temperature for one hour. The growth medium was incubated at 22° C. in the nucleation chambers and then the temperature was decreased to 10° C. at a rate of 0.5° C./min. After nucleation was detected (1.15× baseline voltage), the temperature was increased to the final growth temperature of 28° C. at a rate of 0.5° C./min. A small population of crystals measuring 0.2 mm×0.2 mm was obtained after four days of incubation at the final growth temperature.

With reference to FIG. 24(b), bovine insulin (Sigma, 8 mg) was dissolved in 1.5 mL of 0.02M HCl. The following reagnets were added in the order liseted: 150 microliters of 0.15M zinc acetate, 750 microliters of 0.2M trisodium citrate, 510 micorliters of acetone, 90 microliters of water, and 0.18 g of sodium chloride. The pH was adjusted to 6.4 and the solution was heated for a few minutes at 40° C. to ensure that all medium components were in solution. The growth medium was centrifuged for one hour at 40° C., filtered over an Anotop filter and then incubated at 40° C. in the nucleation chambers for one hour. Then the temperature was decreased from 40° C. to 10° C. at a rate of 0.02° C./min. After nucleation was detected (1.15× baseline voltage), the temperature was increased to the final growth temperature of 28° C. at a rate of 0.5° C./min. This resulted in a large population of 0.1 mm×0.1 mm crystals by day 6 of incubation at the final growth temperature With reference to FIG. 24(c), porcine insulin (Sigma, 10 mg) was dissolved in 1.5 mL of 0.02M HCl. The following reagents were added in the order listed: 150 microliters of 0.15M zinc acetate, 750 microliters of 0.2M trisodium citrate, 510 microliters of acetone, 90 microliters of water, and 0.18 g of sodium chloride. The pH was increased to ~9 with microliter amounts of dilute sodium hydroxide to solubilize all components and then the solution was backtitrated to pH=6.4 with dilute hydrochloric acid. The solution was centrifuged for one hour at 40° C., filtered over an Anotop filter, incubated at 22° C. in the nucleation chamber for one hour and then the temperature was decreased from 40° C. to 10° C. at a rate of 0.5° C./min. After nucleation was detected (this was set at 1.15× baseline voltage that was accumulated during the one hour incubation at 40° C.), the temperature was increased to the final growth temperature of 28° C. at a rate of 0.5° C./min. A small population of 0.25 mm×0.20 mm crystals were obtained after one day at the final growth temperature.

Figure 24D:
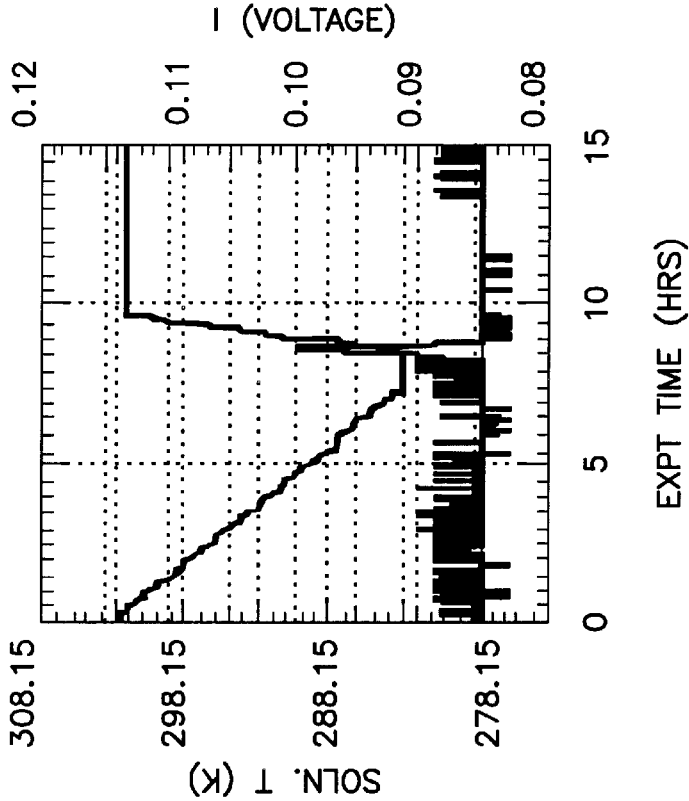
Figure 24C:
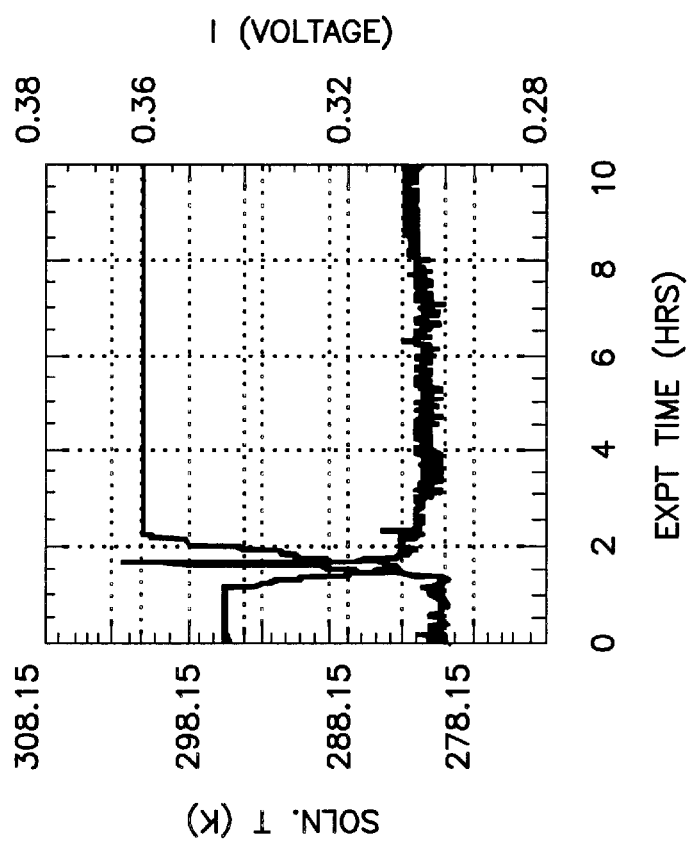

With reference to FIG. 24(d), porcine insulin (Sigma, 10 mg) was dissolved in 1.5 mL of 0.02M HCl. The following reagents were added in the order listed: 150 microliters of 0.15M zinc acetate, 750 microliters of 0.2M trisodium citrate, 510 microliters of acetone, 90 microliters of water, and 0.18 g of solid sodium chloride. The pH was increased by the addition of microliter amounts of dilte sodim hydroxide to solubilize all medium components and then backtitrated with microliter amounts of dilute hydrochloric acid to pH=6.4. The mediuk was centrifuged at room temperature, filtered over an Anotop filter and incubated at 30° C. for one hour in the nucleation chambers. The temperature was decreased to the nucleation temperature of 10° C. at a rate of 0.05° C./min. After nucleation was detected (1.15× baseline voltage), the temperature was increased to the final growth temperature of 28° C. at a rate of 0.25° C./min. A small population of crystals measuring 0.3 mm×0.3 mm was obtained after five days of incubation at the final growth temperature.

Figure 25:
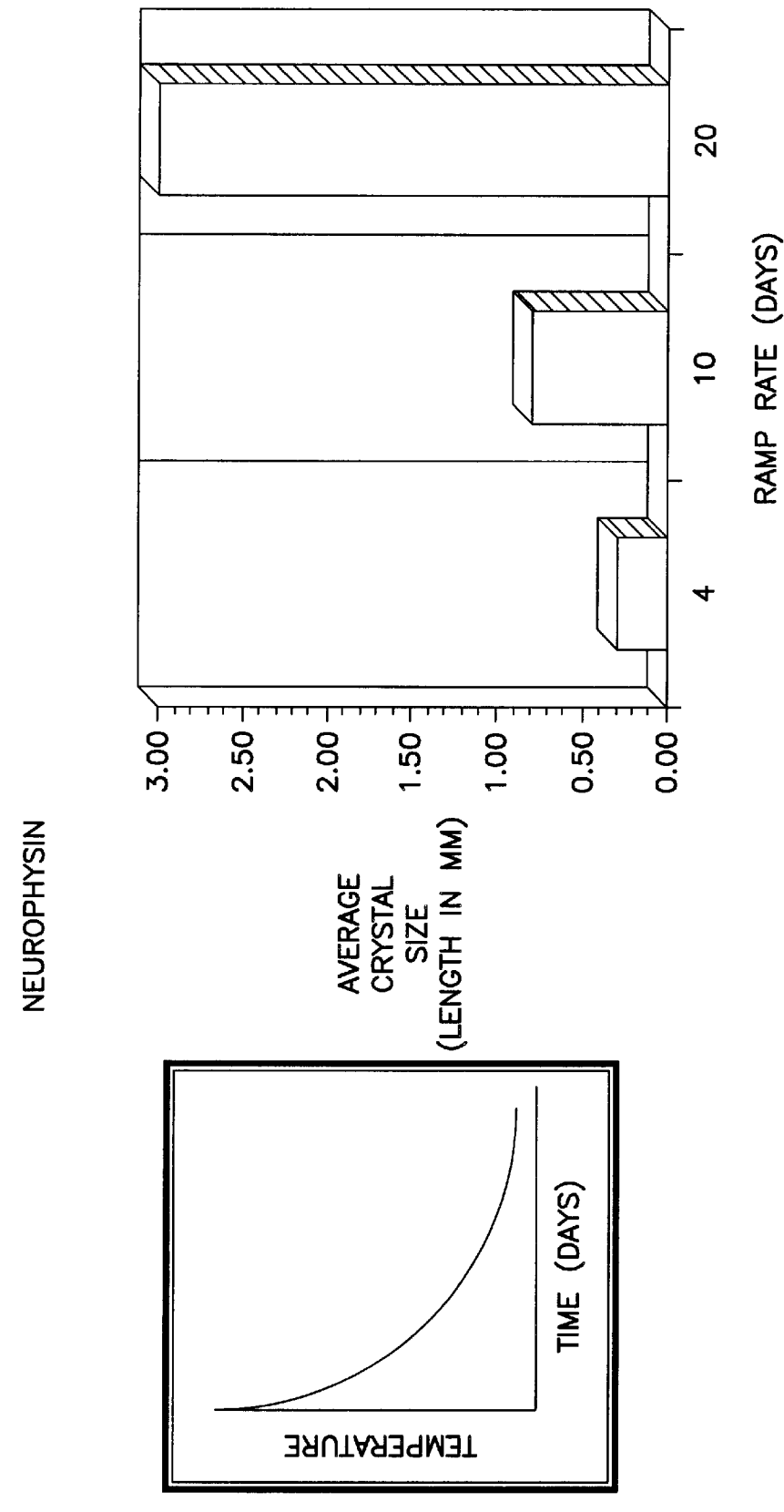
FIG. 25 shows temperature crystallization data for the protein neurophysin.

FIG. 25 presents data collected from the temperature induction system of Example 3 on the protein, neurophysin. As the ramp rate decreased, or in other words, as the temperature change occurred over a longer period of time, the crystal size increased.

Thus, static laser light scattering is one example of a system that can be used to detect the aggregation of lysozyme and insulin, and the particle size response of these proteins to changes in temperature is rapid. This allows a decoupling of the nucleation and growth stages of crystal growth. In addition, these results demonstrate that temperature can have a profound effect on the population and size of crystals that are obtained for a given experiment. The rate at which the temperature is changed as well as the target nucleation temperature both can affect the size and population of crystals obtained for a given protein. This effect has been examined for several different proteins including lysozyme, insulin and insulin complexes (from different species), and neurophysin. Results from the temperature induction studies and systems indicate it is possible to demonstrate that crystal nucleation can be detected by laser light scattering in microliter volume samples and can be reversed via temperature change (σ decreased, where σ is the ratio of protein concentration over protein solubility). The results show that nucleation temperature varies in a qualitative way that is predictable and reproducible as a function of protein solution variables. They also demonstrate that it is possible to investigate various post-nucleation growth profiles by dynamically controlling temperature to change σ. In the temperature induction studies, we found that the change in the baseline scattering definition that triggers a change in temperature profile(s) varied from 15% to 45% of the light scattering background. In these studies, $T_{nuc}$ definition is the target nucleation temperature. It was found that large aggregate/nuclei were more difficult to dissociate and that lower $T_{nuc}$ definition resulted in fewer, larger crystals.

Figure 26:
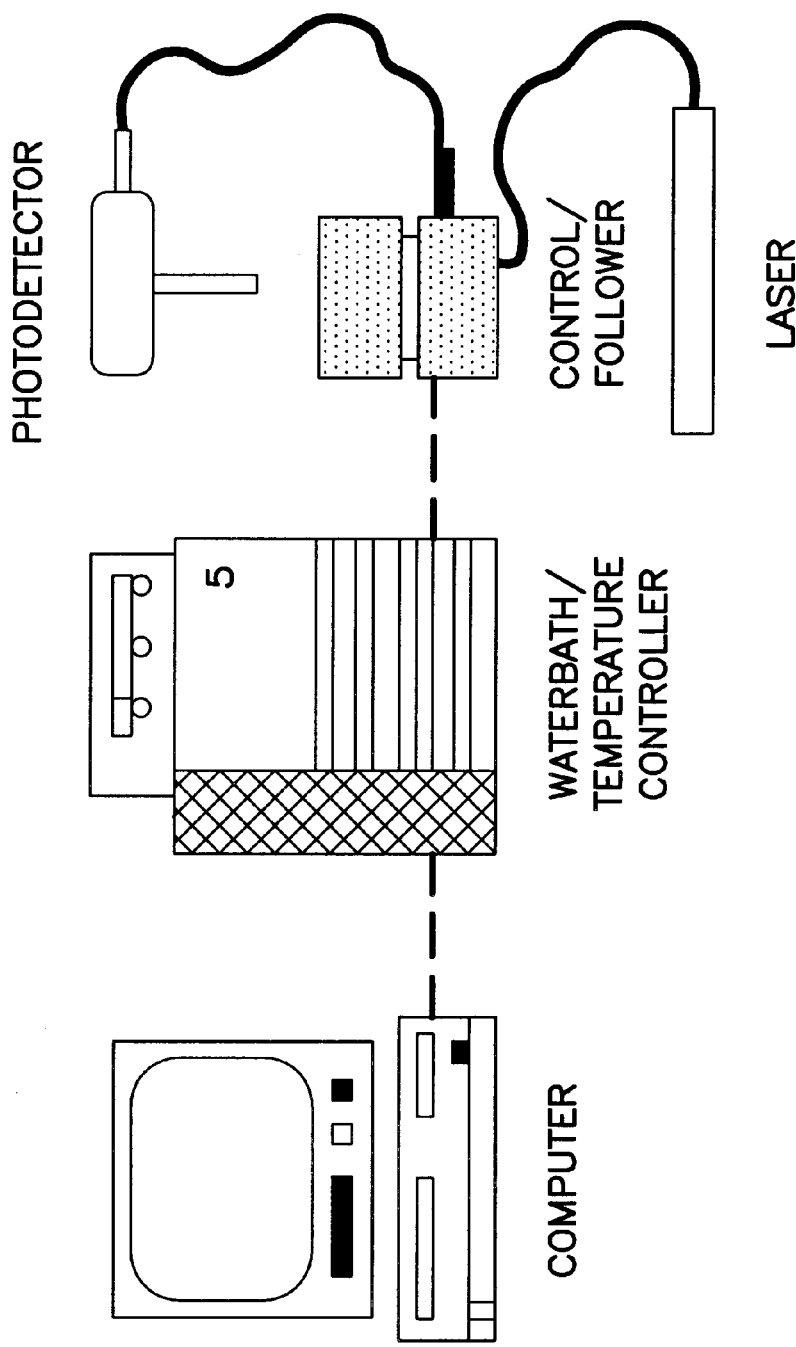
FIG. 26 illustrates a dynamically controlled temperature control/follower system.
Figure 27:
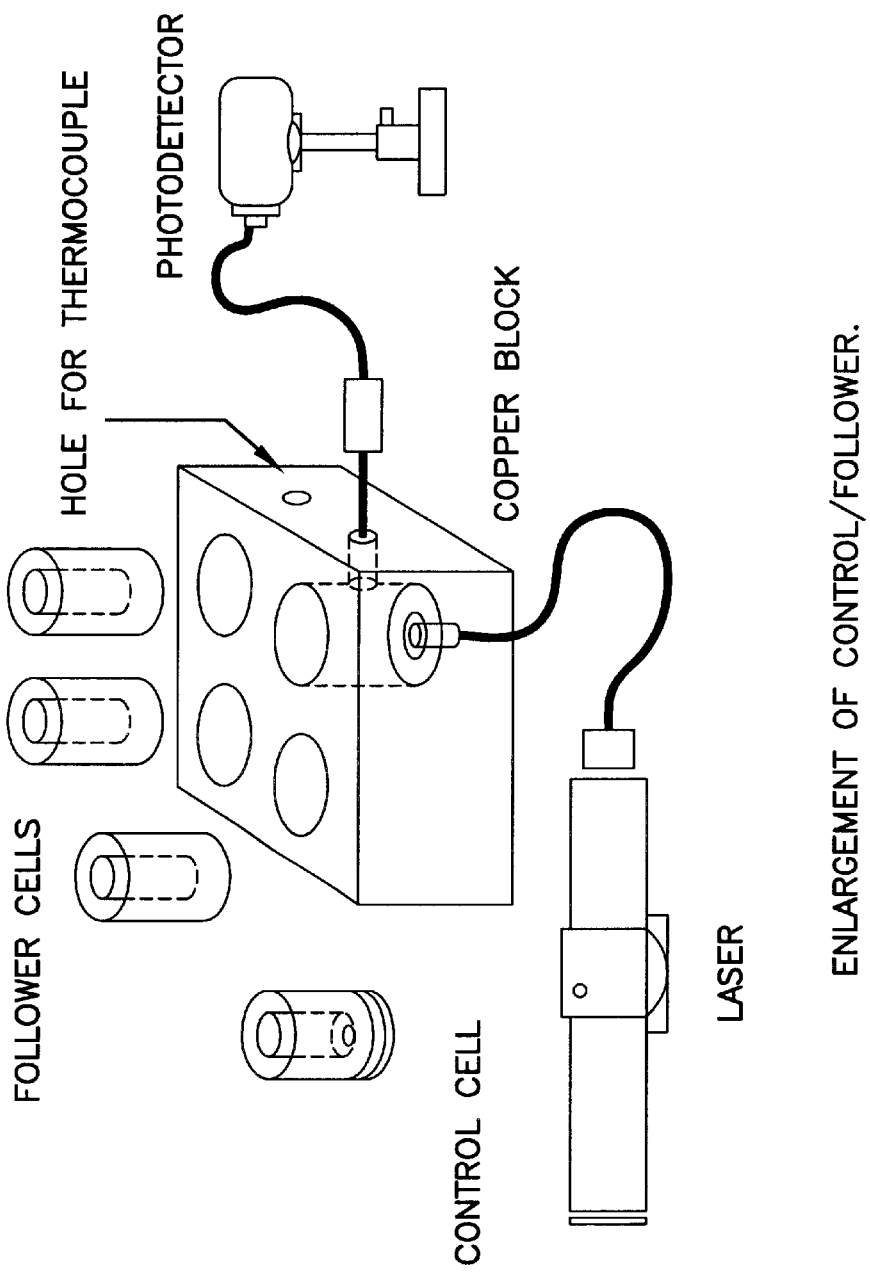
FIG. 27 shows details of the control/follower system.

FIGS. 26 and 27 show a temperature based dynamic control system incorporating the basic technical features described above, but does differ in some of the specific hardware. Temperature is controlled with a programmable water bath while the growth chamber may be a 200 microliter polysulfone cylinder. It includes a control/follower arrangement to investigate the reproducibility of crystals grown by temperature in which the status of one chamber is used to determine the actions taken on other chambers. The control chamber incorporates the static laser light scattering system for detecting aggregation events, while the three follower chambers do not. The crystallization chambers are housed in an insulated container, which circulates water from a programmable water bath to control the temperature. The previously described custom software (SIMPRO or COMPRO) is used to drive the experiments.

A thermocouple provides temperature feedback to the host microcomputer. The incident laser beam enters the control growth chamber from the bottom of the growth chamber through a fiber optic cable. Scattered light is collected at 90° to the incident beam via a second fiber optic cable that is carried to a photodetector. Foam insulation surrounds the assembly to maintain a given temperature during a reaction.

EXAMPLE 4

Hen egg white lysozyme was obtained from Calbiochem. NaCl, NaOAc, and glacial acetic acid were obtained from Fisher Scientific. A 50 mM acetate buffer was prepared by dissolving NaOAc in 18 Mohm deionized water. The pH was adjusted to 4.7 using glacial acetic acid. Lysozyme was dissolved in buffer and then dialyzed several times against fresh buffer to remove any salt from the source protein. This solution was then concentrated using Amicon microconcentrators to create a stock solution at 120 mg/mL. A 4% (w/v) stock solution of NaCl was prepared by dissolving the salt in buffer. Equal volumes of the stock protein and NaCl solutions were mixed and centrifuged for one hour. The supernatant was then filtered through a 0.2 micron Anotop filter.

160 microliters of the growth solution is deployed into each growth cell, and then the cells are inserted into the chamber assembly and sealed with caps. From the initial temperature T1 (22° C. in this example) the temperature is ramped at some rate R1 (0.5° C./minute down in this example) towards the target nucleation temperature T2 (3° C. in this example). If nucleation is detected by the LLS system, then the temperature ramp is modified before reaching the target temperature. Upon detecting nucleation or reaching the target nucleation temperature, the temperature is then ramped at some rate R2 (0.5° C./minute up in this example) to a final growth temperature T3 (13° C. in this example). Other more complex temperature profiles are possible as defined by the experimenter.

Figure 28B:
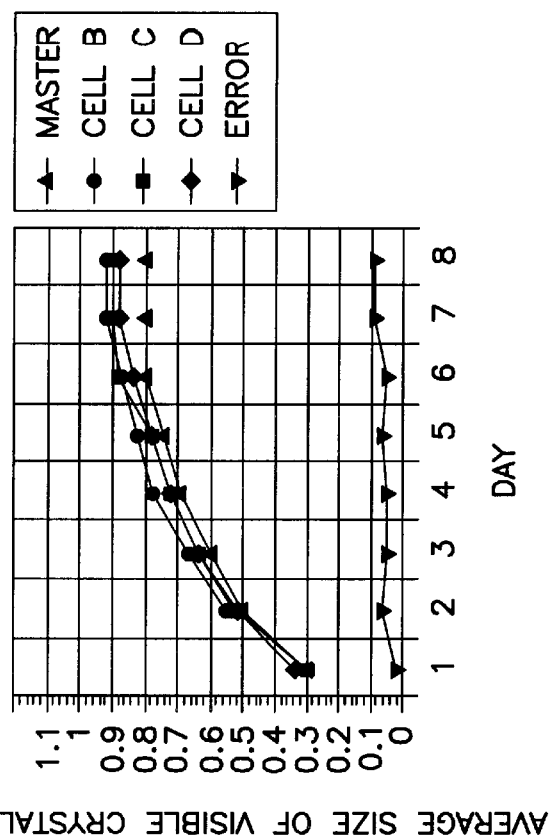
FIGS. 28(a) and (b) show results from crystallization of lysozyme with a modified version of the temperature crystal growth method.
Figure 28A:
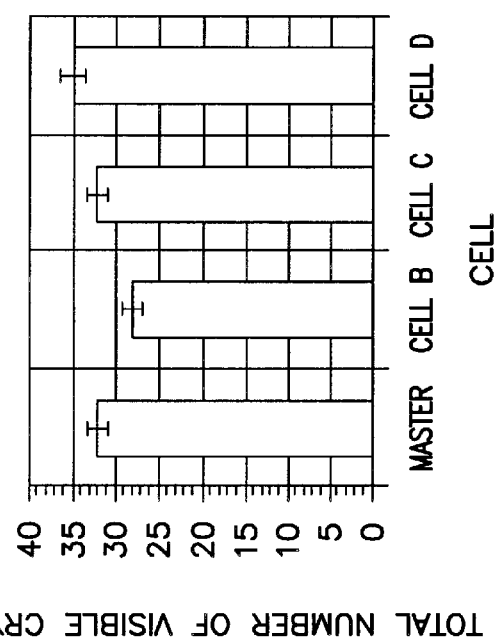

Initial experiments with this system were performed with two proteins, lysozyme and thaumatin. The results obtained using this system demonstrate good reproducibility between cells run under identical conditions (FIG. 28). Both the number and size of crystals obtained are similar in all four cells. This demonstrates that a control/follower arrangement can be used with success to grow crystals of comparable size and quantity in several different cells while actively monitoring (with static laser light scattering, LLS) only one of the identically controlled cells. This approach eliminates the need to use multiple sensors to control duplicate (identical) experiments.

It can be seen that the present invention can utilize two methods, vapor diffusion and temperature, to control the nucleation and growth of protein crystals. Either method can be used successfully to gain control over the crystal growth process in a manner previously unavailable.

The vapor diffusion approach has shown that varying the evaporation rate of the growth solutions systematically affects the size and number of the crystals obtained. Faster evaporation rates generally lead to larger populations of smaller crystals than slower evaporation rates. Inclusion of a non-invasive sensor (LLS) has been used to detect aggregation, at which point the initial evaporation rate is modified, resulting in a smaller population of larger crystals than obtained without dynamic response. These results are likely related to the length of time that a given growth solution resides at a supersaturation level where nucleation occurs.

The temperature based protein crystal growth systems follow an approach where the crystal growth solution is maintained in a container, rather than as a hanging drop, and use precise control of temperature via TED's or a water bath to induce nucleation and control crystal growth. A static laser light scattering system is used as a diagnostic to detect aggregation and the temperature modified to optimize crystal growth. A control/follower configuration has been used whereby information obtained by monitoring one chamber can be used to effect similar results in the remaining chambers.

Figure 29:
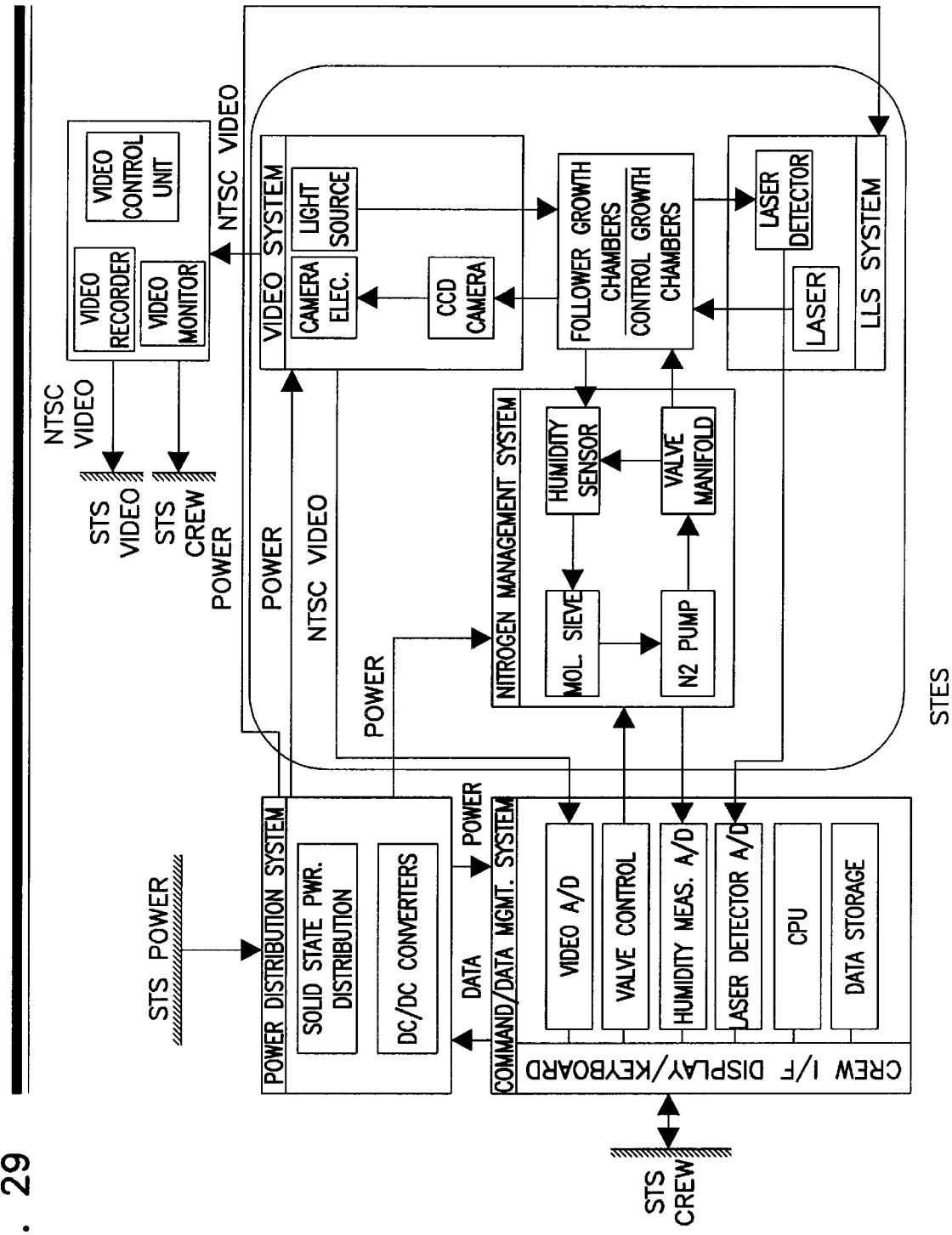
FIG. 29 is a diagram of an example of an interface between the Space Shuttle (STS) and a vapor diffusion dynamically controlled protein crystal growth system.
Figure 30:
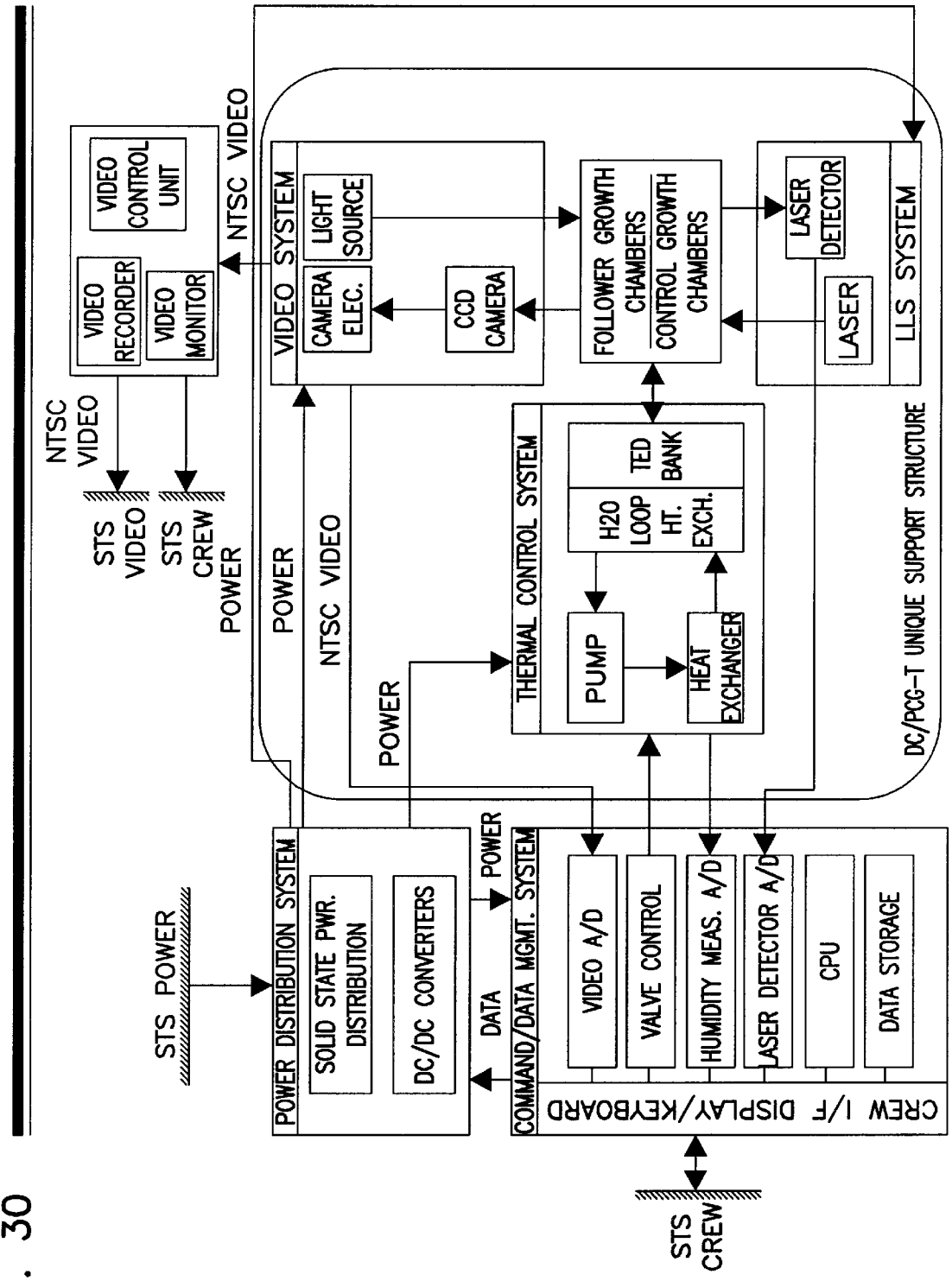
FIG. 30 is a diagram of an example of an interface between the Space Shuttle (STS) and a temperature induction dynamically controlled protein crystal growth system.

While the present invention is useful for terrestial crystal growth, development of these systems for microgravity studies should improve the success of protein crystal growth on the space shuttle and/or the international Space Station. The flight experiment would be via a dynamically controlled protein crystal growth technique which uses either of the two methods, vapor equilibration or temperature, to control and optimize the crystallization process. This would be accomplished by controlling supersaturation prior to and after the nucleation event, which can be detected via laser light scattering. Video information can also be used to evaluate crystal data so that subsequent experiments could be altered in an attempt to optimize results. FIGS. 29 and 30 are respectively diagrams of examples of the system interfaces for the vapor diffusion systems (DC/PCG-V) and the temperature systems (DC/PCG-T) with the Space Shuttle (STS). The systems used for space shuttle work should be made with components approved under the relevant NASA guidelines. In FIG. 26, the indication STES stands for Single Thermal Enclosure System, which also is known as CRIM.

While a detailed description has been provided above, the present invention is not limited thereto, but rather is defined by the following claims.

What is claimed is:

1. An apparatus for crystal growth, comprising:
   a growth chamber comprising a first section for containing a solution comprising a substance to be crystallized and a solvent for the substance to be crystallized and a second second divided from the first section, whereby evaporation of the solvent from the solution causes crystallization of the substance to be crystallized from solution;
   a gas flow source in communication with the second of the growth chamber, for providing a gas flow to remove evaporated solvent vapor from the growth chamber; and
   a gas flow source control for changing the gas flow rate to the growth chamber.

2. An apparatus according to claim 1, further comprising an aggregation or nucleation detector for determining the onset of aggregation or nucleation in the solution and creating a signal for the gas flow source control to change the gas flow rate in response to the onset of aggregation or nucleation.

3. An apparatus according to claim 1, further comprising a barrier between the first and second sections for preventing any substantial impingement of the gas flow on the solution in the first section.

4. An apparatus according to claim 3, wherein the barrier is a plate with a central opening.

5. An apparatus according to claim 3, wherein the barrier is a membrane that is permeable to the solvent vapor.

6. An apparatus according to claim 1, wherein the gas is nitrogen.

7. An apparatus according to claim 1, further comprising a detector for solvent vapor removed from the growth chamber.

8. An apparatus according to claim 1, wherein the solvent is water and the apparatus comprises a sensor for measuring humidity of gas removed from the growth chamber.

9. An apparatus according to claim 1, wherein the substance to be crystallized is selected from the group consisting of a protein, a polypeptide, a nucleic acid, a virus and a virus fragment.

10. A method of growing crystals, comprising:
    providing in a first section of a growth chamber a solution comprising a solvent in which a substance to be crystallized is dissolved, whereby solvent can evaporate from the solution;
    supplying a gas flow to a second section of a growth chamber, the second section being divided from the first section, to remove evaporated solvent from the growth chamber, whereby evaporation of the solvent from the solution causes crystallization of the substance to be crystallized from the solution; and
    analyzing the solution during evaporation of the solvent to detect an onset of nucleation and changing the gas flow rate upon detection of the onset nucleation.

11. The method of claim 10, wherein direct infringement of the gas flow on the solution is substantially prevented.

12. The method of claim 10, wherein the substance to be crystallized is selected from the group consisting of a protein, a polypeptide, a nucleic acid, a virus and a virus fragment.

13. The method of claim 12, wherein the substance to be crystallized is a protein.

14. The method of claim 12, wherein the substance to be crystallized is a polypeptide.

15. The method of claim 12, wherein the substance to be crystallized is a nucleic acid.

16. The method of claim 12, wherein the substance to be crystallized is a virus.

17. The method of claim 12, wherein the substance to be crystallized is a virus fragment.

* * * * *